US006885965B2

(12) United States Patent
Butler et al.

(10) Patent No.: US 6,885,965 B2
(45) Date of Patent: Apr. 26, 2005

(54) PROCESSING SYSTEM FOR REMOTE CHEMICAL IDENTIFICATION

(75) Inventors: Matthew Butler, Baton Rouge, LA (US); Grant Plummer, Durham, NC (US)

(73) Assignee: First Responder Systems Technologies, LLC, Baton Rouge, LA (US)

( * ) Notice: Subject to any disclaimer, the term of this patent is extended or adjusted under 35 U.S.C. 154(b) by 0 days.

(21) Appl. No.: 10/444,045

(22) Filed: May 22, 2003

(65) Prior Publication Data

US 2004/0111232 A1 Jun. 10, 2004

Related U.S. Application Data

(60) Provisional application No. 60/382,435, filed on May 22, 2002.

(51) Int. Cl.[7] ........................... G01B 9/02; G06F 15/46; G06F 15/00
(52) U.S. Cl. ....................... 702/130; 356/451; 374/131; 702/22; 702/23
(58) Field of Search ............................. 702/22, 23, 27, 702/28, 99, 130; 356/51, 451, 311; 250/338.5, 339, 341; 600/316; 607/88; 374/131

(56) References Cited

U.S. PATENT DOCUMENTS

| | | |
|---|---|---|
| 4,555,627 A | 11/1985 | McRae, Jr. |
| 4,676,642 A | 6/1987 | French |
| 4,772,789 A | 9/1988 | Maram et al. |
| 4,790,669 A * | 12/1988 | Christensen ................ 374/131 |
| 4,795,253 A | 1/1989 | Sandridge et al. |
| 4,999,498 A | 3/1991 | Hunt et al. |
| 5,241,179 A | 8/1993 | Carrieri |
| 5,262,961 A * | 11/1993 | Farone ......................... 702/23 |
| 5,294,796 A | 3/1994 | Fee |
| 5,298,751 A | 3/1994 | Fee et al. |
| 5,373,160 A | 12/1994 | Taylor |
| 5,451,787 A | 9/1995 | Taylor |
| 5,637,872 A | 6/1997 | Tulip |
| 5,748,325 A | 5/1998 | Tulip |
| 5,790,250 A | 8/1998 | Wang et al. |
| 5,831,267 A | 11/1998 | Jack et al. |
| 5,959,730 A | 9/1999 | Wang et al. |
| 5,982,486 A | 11/1999 | Wang |
| 6,010,665 A | 1/2000 | Dosoretz et al. |
| 6,711,503 B1 * | 3/2004 | Haaland ....................... 702/22 |

OTHER PUBLICATIONS

Charles Chaffin, "The Development of Sampling Strategies for Open–Path FT–IR Monitoring of Fugitive Emissions", MIDAC Corporation, AP–110.

Jack Demirgian, "Detection of Fugitive Emissions Using Passive–Remote FTIR Spectroscopy", MIDAC Corporation, AP–112.

W.C. Hamilton, Statistics in Physical Science, Ronald Press Co., New York, 1964 (Chapter 4, partial).

*Assistant Examiner*—John Le

(74) *Attorney, Agent, or Firm*—Jones, Walker, Waechter, Poitever, Carrere & Denegre, L.L.P.

(Continued)

*Primary Examiner*—John Barlow

(57) ABSTRACT

A fourth embodiment of the present invention is a method of generating a temperature compensated absorbance spectrum. The method includes the steps of: a. providing a sample spectrum and an estimated temperature of a backdrop object; b. from a set of known temperature spectra related to a known background temperature, selecting at least two known temperature spectra representing a background temperature above and below the estimated temperature; c. comparing the sample spectrum to the known temperature spectra in order to determine a sample background spectrum; and d. calculating an absorbance spectrum from the sample spectrum and the background spectrum.

24 Claims, 30 Drawing Sheets

OTHER PUBLICATIONS

D.M. Haaland & R.G. Easterling, "Improved Sensitivity of Infrared Spectroscopy by the Application of Least Squares Methods," Appl. Spectrosc., vol. 34, No. 5, pp. 539–548, 1980.

D.M. Haaland & R.G. Easterling, "Application of New Least–Squares Methods for the Quantitative Infrared Analysis of Multicomponent Samples," Appl. Spectrosc., vol. 36, No. 6, pp., 665–673, 1982.

D.M. Haaland & R.G. Easterling & D.A. Vopicka, "Multivariate Least–Squares Methods Applied to the Quantitative Spectral Analysis of Multicomponent Samples," Appl. Spectrosc., vol. 39, No. 1, pp. 73–84, 1985.

Hue Phan & Jerry Auth, "Measurements of Chemical Emmisions Using FTIR Spectroscopy",American Laboratory News, Aug. 1993.

T.L. Marshall, C.T. Chaffin, R.M. Hammaker & W.G. Fateley, "An Introduction to Open–Path Fourier Transform Infrared Atmospheric Monitoring", Environmental Science & Technology, Dec. 23, 1993.

Charles Chaffin, Jr. & Tim Marshall, "Distinguishing Benzene's 674 cm–1 –Absorption Band From Interferences in Open–Path FTIR Spectra", American Environmental Laboratoy, Apr. 1995.

Robert J. Yokelson, David W.T. Griffith & Darold E. Ward, "Open–Path Fourier Transform Infrared Studies of Large–Scale Laboratory Biomass Fires," Journal of Geophysical Research, vol. 101, No. D15, pp. 21,067–21,080, Sep. 20, 1996.

Robert J. Yokelson, Ronald Susott, Darold E. Ward & James Reardon, "Emissions From Smoldering Combustion of Biomass Measured by Open–path FTIR", Journal of Geophysical Research, Oct. 7, 1996.

Mike Dunne, "Universtiy Helps Build Device to ID Chemical Fumes", Baton Rouge Morning Advocate, Jul. 29, 1998.

George Lane, "Utilization with Infrared Remote Sensing in Emergency Response", Division of Environmental Chemistry Preprints of Extended Abstracts, vol. 39, No. 2, Aug. 1999.

"Air Quality Monitoring—RAM 2000 System Software", www.nycedo.com, Nov. 15, 2001.

* cited by examiner

CHEMICAL PROPERTY DATABASE

| | VISIBLE VAPOR | VAPOR DENSITY | VAPOR COLOR | SMELL | HYDROLYSIS SMELL | HYDROLYSIS COLOR | HYDROLYSIS DENSITY | MW | PICs |
|---|---|---|---|---|---|---|---|---|---|
| COMPOUND A | NO | VP<1 | N/A | PUNGENT | | | | N/A | |
| COMPOUND B | YES | VP<1 | GREENISH YELLOW | PUNGENT BLEACH-LIKE | | | | | |
| COMPOUND C | | | | | | | | | |

*FIG. 6*

PROCESSING SYSTEM FOR REMOTE CHEMICAL IDENTIFICATION

This is a non-provisional application claiming the benefit of provisional application Ser. No. 60/382,435 filed on May 22, 2002.

I. BACKGROUND OF INVENTION

The present invention relates to devices and methods for identifying unknown chemical compounds under field conditions. In particular, the present invention relates to devices and methods of using remote passive infra-red spectroscopy, in addition to spectral data, to identify the chemical compounds.

There are often instances where emergency response personnel ("first responders") or military personnel are called to an accident scene or other incident where some type of chemical has been release and are confronted with gaseous cloud or plume, the chemical contents of which are unknown. Such situations can occur when railroad tank cars or highway transport tank trailers carrying chemicals are involved in an accident or when an accidental chemical release occurs at a chemical manufacturing facility. Obviously, knowing the contents of the plume is critical to decisions concerning how to contain the emergency, what protective gear is required, and whether there is a need to evacuate the local population. Methods of using remote passive infra-red (IR) spectrometers to attempt to identify the chemical compounds in a gaseous plume are known in the art. As used herein, the term "passive" implies that the spectrometer employs no specialized source of infrared photons (as opposed to "active" systems, which employ photons from optically optimized, high-temperature sources). The term "remote" indicates that the sample gases of interest are external to the spectrometer such as a plume at an accident site. Closed path spectroscopy may include extractive systems, which interrogate samples in an absorption cell, or use a well known photon source and a well known path length.

The general concept of IR spectroscopy in this situation is illustrated in FIG. 1. A passive spectrometer 101 will be positioned such that the gaseous plume 103 is between the spectrometer and some background object 105, which will provide a source of IR energy. In the case where the background 105 is significantly warmer than the plume 103, IR energy emitting from background 105 will pass through plume 103 and be recorded by spectrometer 101. Because different chemical compounds tend to absorb different wavelengths of IR energy, a measurement of the relative intensities of different frequencies of IR energy received at the spectrometer will provide information which may be used to identify the compounds in plume 103. In some cases, where the plume is warmer than its surroundings, the compounds within the plume may themselves emit (rather than absorb) at these IR frequencies. This absorbance is linearly related to the gaseous concentrations through the Beer-Lambert relation, or "Beer's Law." When infrared radiation passes linearly through a gas sample for a distance L, its initial intensity ($I_0$) is decreased through gaseous absorption to the level (I) measured at the spectrometer. Beer's Law states that the absorbance at each infrared frequency is defined by the relationship:

$$A \equiv -\log_{10}\left(\frac{I}{I_0}\right) \qquad \text{Eq. (0)}$$

The detailed function of a conventional spectrometer is explained in references such as U.S. Pat. No. 5,982,486, which is incorporated by reference, and need not be detailed herein. It is sufficient to understand from FIG. 2 that the spectrometer will initially create an "interferogram" (step 107) representing the space-domain response of its detector to the infrared radiation incident on the detector. The application of a fast-Fourier transform to the interferogram will form a sample single-beam (step 109) representing the total power incident on the infrared detector as a function of infrared frequency, the latter usually being expressed in units of "wavenumbers", or reciprocal centimeters ($cm^{-1}$). An illustration of a sample single-beam spectrum is seen in the lower trace of FIG. 3.

Because passive IR spectroscopy employs a background source of IR energy, the signals of real interest, namely the relatively narrow absorption and/or emission bands of the gases located between the spectrometer and the backdrop, are superimposed upon the smooth, broad emission spectrum of the background IR source. It is therefore necessary to develop some type of background spectrum. While the present invention's method of forming the background spectrum is described below, the middle trace of FIG. 3 illustrates the background single-beam spectrum graphically which will aid in understanding conceptually the invention's background.

Once the sample single-beam spectrum (step 111) and background single-beam spectrum (step 112) are determined, the sample absorbance spectrum may be calculated. In the notation adopted below, the sample absorbance spectrum (step 117) is defined in terms of the single beam sample spectrum $SB_i^S$ and the single beam background spectrum $SB_i^B$ as:

$$A \equiv -\log_{10}\left(\frac{SB_i^S}{SB_i^B}\right) \qquad \text{Eq. (1)}$$

The upper trace of FIG. 3 illustrates the sample absorbance spectrum.

Once the absorption spectrum for the sample ("sample absorbance spectrum") is created, it can be compared to the know absorption spectra for various chemical compounds ("reference spectra") which may be represented in the sample absorbance spectrum. The reference spectrum of a compound may be considered the graphical representation of the degree of absorbance a chemical compound exhibits at those frequencies at which the compound absorbs IR radiation. Figuratively speaking, the reference spectrum is the IR "figure print" of a chemical compound. There are many methods for determining how closely a part of the sample absorbance spectrum matches a reference spectrum and thus with how much confidence it can be concluded that the reference chemical (i.e. the compound represented by the reference spectrum) exists in the sample gas. One method of comparing a sample absorbance spectrum to one or more reference spectra, is the utilization of a classical least squares analysis.

The use of Classical Least Squares (CLS) analyses is known in the art and has been used in spectral analysis as evidenced by publications such as D. M. Haaland and R. G. Easterling, "Improved Sensitivity of Infrared Spectroscopy by the Application of Least Squares Methods," *Appl. Spec-* trosc. 34(5):539–548 (1980); D. M. Haaland and R. G. Easterling, "Application of New Least-Squares Methods for the Quantitative Infrared Analysis of Multicomponent Samples," *Appl. Spectrosc.* 36(6):665–673 (1982); D. M. Haaland, R. G. Easterling and D. A. Vopicka, "Multivariate Least-Squares Methods Applied to the Quantitative Spectral Analysis of Multicomponent Samples," *Appl. Spectrosc.* 39(1):73–84 (1985); W. C. Hamilton, *Statistics in Physical Science*, Ronald Press Co., New York, 1964, Chapter 4 and references therein; and U.S. Pat. No. 5,982,486, all of which are incorporated by reference herein. While a full mathematical description of CLS is disclosed in the above references, a brief description, particularly in terms of matrix manipulation, will provide a useful background.

CLS analyses are generally useful in estimating the solutions of an over-determined system of linear equations; such a system of equations can always be represented by a matrix equation of the form $$A = DX + E \quad \text{Eq. (2)}$$

where:

| | | |
|---|---|---|
| A | = | a set of N measured data, represented by a row vector |
| X | = | a set of M parameters to be estimated, represented by a column vector |
| D | = | The "design matrix," with N rows and M columns, describing the linear mathematical relationship between the measured data A and the parameters X |
| E | = | The error in the linear model for each of the measured data, represented by a row vector of length N. |

As it relates to the comparison of a sample spectrum to one or more reference spectra, the matrix:

$$A = [A_1^S, A_2^S, \ldots A_N^S],$$

will represent the sample spectrum with each member $A_i^S$ of A representing an intensity value at the wavenumber $v_i$ over the frequency range $[v_1, v_2, \ldots v_N]$. In the design matrix:

$$D = \begin{pmatrix} A_{11}^R & A_{12}^R & \cdot & A_{1M}^R & 1 & v_1 \\ A_{21}^R & A_{22}^R & \cdot & \cdot & 1 & v_2 \\ \cdot & \cdot & \cdot & \cdot & \cdot & \cdot \\ A_{NI}^R & A_{N2}^R & \cdot & A_{NM}^R & 1 & v_N \end{pmatrix} \quad \text{Eq. (3)}$$

each column will represent a reference spectrum, with each member of a column $A_{ij}^R$ (using the first column as an example) representing an intensity value of the reference spectrum over the same frequency range as the absorption spectrum.

In the case N>M (that is, when the number of measured data exceeds the number of parameters to be estimated), the system of equations described in Equation 2 is referred to as "over-determined." In this case, which pertains to all the CLS applications described here, there is no unique solution to Equation 2. However, it possible in this case to form estimates of the parameters $\overline{X}$ and to characterize the accuracy of those estimates. Such estimates and characterizations may be based on any chosen set of mathematical criteria and constraints. A widely used criterion is to form estimates of the parameters $\overline{X}$ that minimize the "weighted sum of squared residuals" for the model of Equation 2; this sum may (or may not) be defined in such a way as to account for variations in the quality of the measured data $A_i$. Such estimates are broadly referred to as the results of "least squares" techniques, and only such estimates are described in this work. The term "classical least squares" refers to least squares techniques based solely on the linear model described in Equation 2; other least squares techniques, e.g. those referred to as "partial least squares" analyses, often employ additional processing of the data and result in more complex approaches to estimations of the desired parameters $\overline{X}$.

Formally, "classical least squares" estimates are based on the assumptions that the error vector E possesses a joint distribution with zero means and a variance-covariance matrix that $M_f$ of rank N. Many CLS estimates also include the further assumptions that the matrix $M_f$ is known to within a (non-negative) scaling factor $\sigma^2$, i.e. that $$M_f = \sigma^2 \begin{pmatrix} N_{11} & N_{21} & \cdot & N_{NI} \\ N_{12} & N_{22} & \cdot & \cdot \\ \cdot & \cdot & \cdot & \cdot \\ N_{1N} & \cdot & \cdot & N_{NN} \end{pmatrix} = \sigma^2 N \quad \text{Eq. (4)}$$

Practically, Equation 2 embodies the assumption the relative quality of the measured data $A_i$ is known. The relative quality of the data may be quantified by assigning a non-negative "weight" $P_{ii}$ to each $A_i$ where the diagonal weight matrix P is (in general) the matrix inverse of N, i.e.

$$P = N^{-1} \quad \text{Eq. (5)}$$

and therefore, according to Equation 5, that $$P_{ii} = \frac{1}{N_{ii}} \quad \text{Eq. (6)}$$

The type of CLS analyses commonly used in the prior art will be designated "unweighted CLS" in order to distinguish it from a "weighted CLS" analysis described below in the Detailed Description of the invention. Both types of CLS analysis employ the assumptions noted above in conjunction with Equations 4, 5, and 6.

Unweighted CLS analysis is one in which all measured data are assumed to be of equal quality; i.e. in the unweighted case, both the matrices P and N are equal to the identity matrix I. For any estimated set of parameters $\overline{X}$, the residual V is defined as:

$$V = A - D\overline{X} \quad \text{Eq. (7)}$$

and the "weighted sum of squared residuals" is defined as:

$$V^2 \equiv V^t P V = (A - D\overline{X})^t P (A - D\overline{X}) \quad \text{Eq. (8)}$$

where the superscript "t" denotes the matrix transpose.

The following estimate of the parameters $\overline{X}$ exists, is unique, and leads to a minimum in $V^2$ (the "weighted sum of squared residuals"):

$$\overline{X} = (D^t P D)^{-1} D^t P A \quad \text{Eq. (9)}$$

Equation 9 describes the basic CLS parameter estimates which are useful and accurate in a number of applications. However, it is important to note that all CLS analyses also provide useful statistical measures of the uncertainties in the parameter estimates.

In particular, CLS analyses provide a "marginal standard deviation" (MSD) for each parameter estimate. Where the CLS estimate of the variance-covariance matrix is $$\overline{M} = V^2 (D^t P D)^{-1} \quad \text{Eq. (10)}$$

the marginal standard deviation (MSD) associated with each parameter estimate $\bar{X}_j$ is $$\overline{\Delta}_j = \sqrt{\overline{M}_{jj}} \qquad \text{Eq. (11)}$$

The MSD is sometimes referred to as the "1σ uncertainty" in the associated parameter. The relative magnitude of $\bar{X}_j$ and $\bar{\Delta}_j$ is often used as an indicator of the quality of the CLS analysis estimate of the parameter $\bar{X}_j$.

Weighted CLS analysis, which forms part of the invention discussed below, is one in which at least one $P_{ii}$ differs from the other values in the matrix P, that is, when at least one datum $A_i$ is assumed to be of better or worse quality than the other $A_i$.

In addition to the spectrometry aspects of the present invention, this invention also relates both to novel methods for processing spectral data and novel methods of identifying chemical compounds based upon the location of a chemical release and conditions (e.g. colors, smells, and the like) observed at the site of the chemical release. This non-spectral method of identifying potential chemical compounds may be used in combination with or independently of spectral methods. When used in combination with spectral methods, the non-spectral methods will function to identify or aid in identifying an initial list of chemical compounds whose reference spectra will be chosen for comparison with the undetermined sample spectrum.

II. SUMMARY OF INVENTION

One embodiment of the present invention provides a system for remote identification of chemical compounds. The system includes passive infra-red spectrometer, a location identifier, a range finder, and a user interface. The system further includes database having data representing chemical reference spectrums, data associating observable properties with certain chemical compounds, and data associating a location with certain chemical compounds. A computer processor communicates with the spectrometer, the location identifier, the range finder, the user interface, and the database. The system also includes software for comparing data from the spectrometer, the location identifier, and the range finder to data in the database in order to identify the potential presence and concentration of one or more chemical compounds.

Second embodiment of the present invention is a method of determining the temperature of a backdrop object against which a sample spectra is recorded. The method includes the steps of: a. providing a predetermined relationship between a parabolic center frequency and a backdrop temperature, wherein the parabolic center frequency is that of a single beam spectrum of a reference backdrop at a known temperature; b. providing a sample spectra recorded against a backdrop of an unknown temperature; c. determining a best fit parabolic curve of the sample spectra; d. determining a sample parabolic center frequency of the best fit parabolic curve; e. comparing the sample parabolic center frequency to the predetermine relationship of center frequency and backdrop temperature; and f. estimating a temperature of the backdrop based upon the comparison.

A third embodiment of the present invention is a method of generating a background spectrum for use in spectral analysis. The method includes the steps of: a. providing a sample spectrum and an estimated temperature of a background object; b. from a set of known temperature spectra related to a known background temperature, selecting at least two known temperature spectra representing a background temperature above and below the estimated temperature; and c. comparing the sample spectrum to the known temperature spectra in order to determine a sample background spectra.

A fourth embodiment of the present invention is a method of generating a temperature compensated absorbance spectrum. The method includes the steps of: a. providing a sample spectrum and an estimated temperature of a backdrop object; b. from a set of known temperature spectra related to a known background temperature, selecting at least two known temperature spectra representing a background temperature above and below the estimated temperature; c. comparing the sample spectrum to the known temperature spectra in order to determine a sample background spectrum; and d. calculating an absorbance spectrum from the sample spectrum and the background spectrum.

A fifth embodiment of the present invention is a method of identifying a chemical represented in an absorbance spectrum. The method includes the steps of: a. providing a sample absorbance spectrum; and b. comparing the absorbance spectrum to spectra for CO2 and H2O and to at least one chemical reference spectrum in order to identify a chemical represented in said absorbance spectrum.

A sixth embodiment of the present invention is a computer system for identifying chemical compounds using observable characteristics. The system includes a chemical database associating predefined characteristics and properties with a plurality of chemical compounds and a user interface accepting input of observable characteristics. The system further includes a processor operating on software directing the processor to identify chemical compounds in the database which correspond with the observable characteristics.

A seventh embodiment of the present invention is a computer system for identifying chemical compounds based upon a location where the compounds are observed. This system includes a chemical/location database associating at least one chemical compound with an assigned map location of the compound and a location input for entering a system location into the system. A processor operates on software which directs the processor to identify chemical compounds in the database which correspond with the system location.

III. BRIEF DESCRIPTION OF THE DRAWINGS

FIG. 1 is a conceptual illustration of a spectrometer, chemical compound cloud and background temperature source.

FIG. 2 figuratively illustrates the prior art signal processing steps for obtaining an interferogram and converting it to an absorption spectrum.

FIG. 6 is a schematic representation of the chemical properties database of the present invention.

IV. DETAILED DESCRIPTION OF THE INVENTION

1. Non-Spectral Identification of Compounds

As mentioned above, the present invention relates not only to novel equipment and methods for processing spectral data, it also relates novel methods of identifying chemical compounds based upon "non-spectral" characteristics such as the location of a chemical release or conditions (e.g. colors, smells, and the like) observed at the site of the chemical release.

Figure 1:
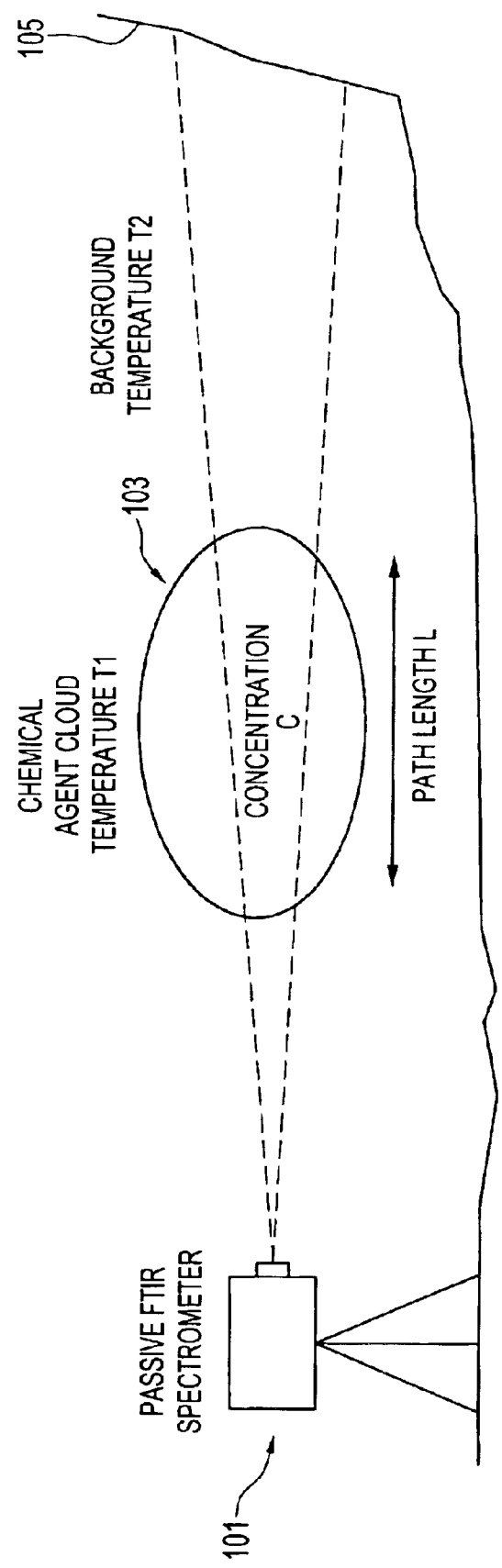
Figure 2:
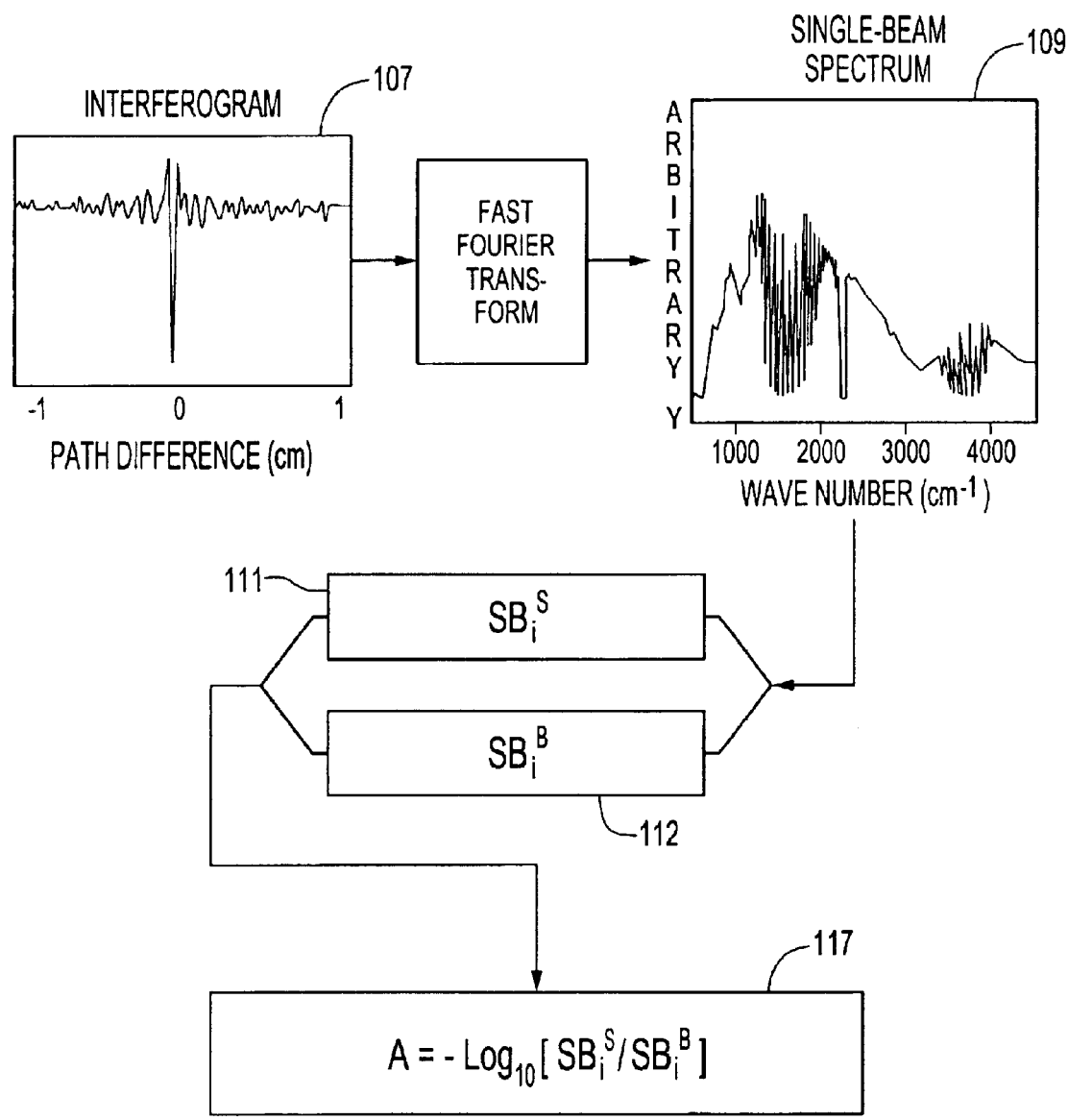
Figure 3:
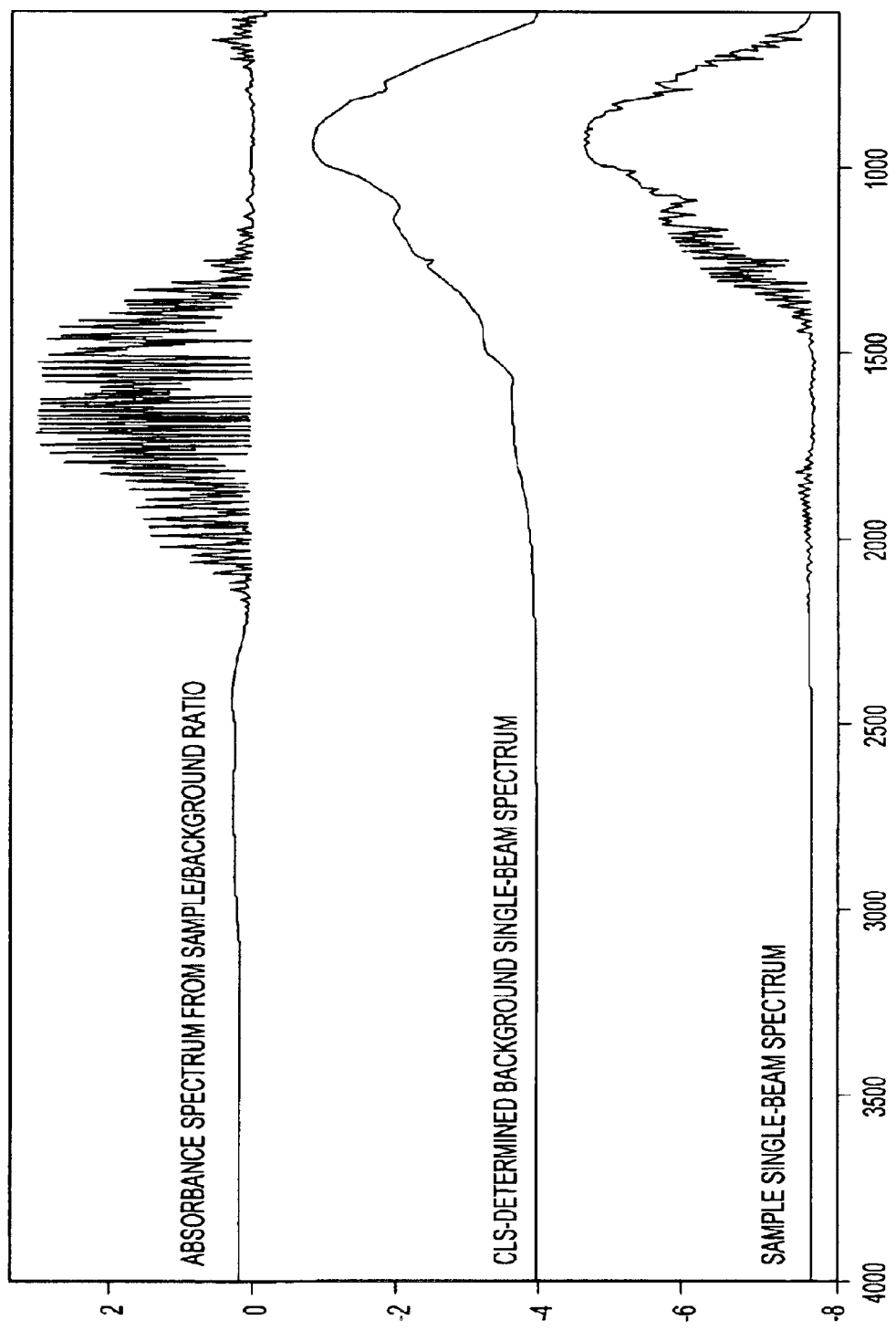
FIG. 3 represents three different spectrum curves related to the present invention.
Figure 4:
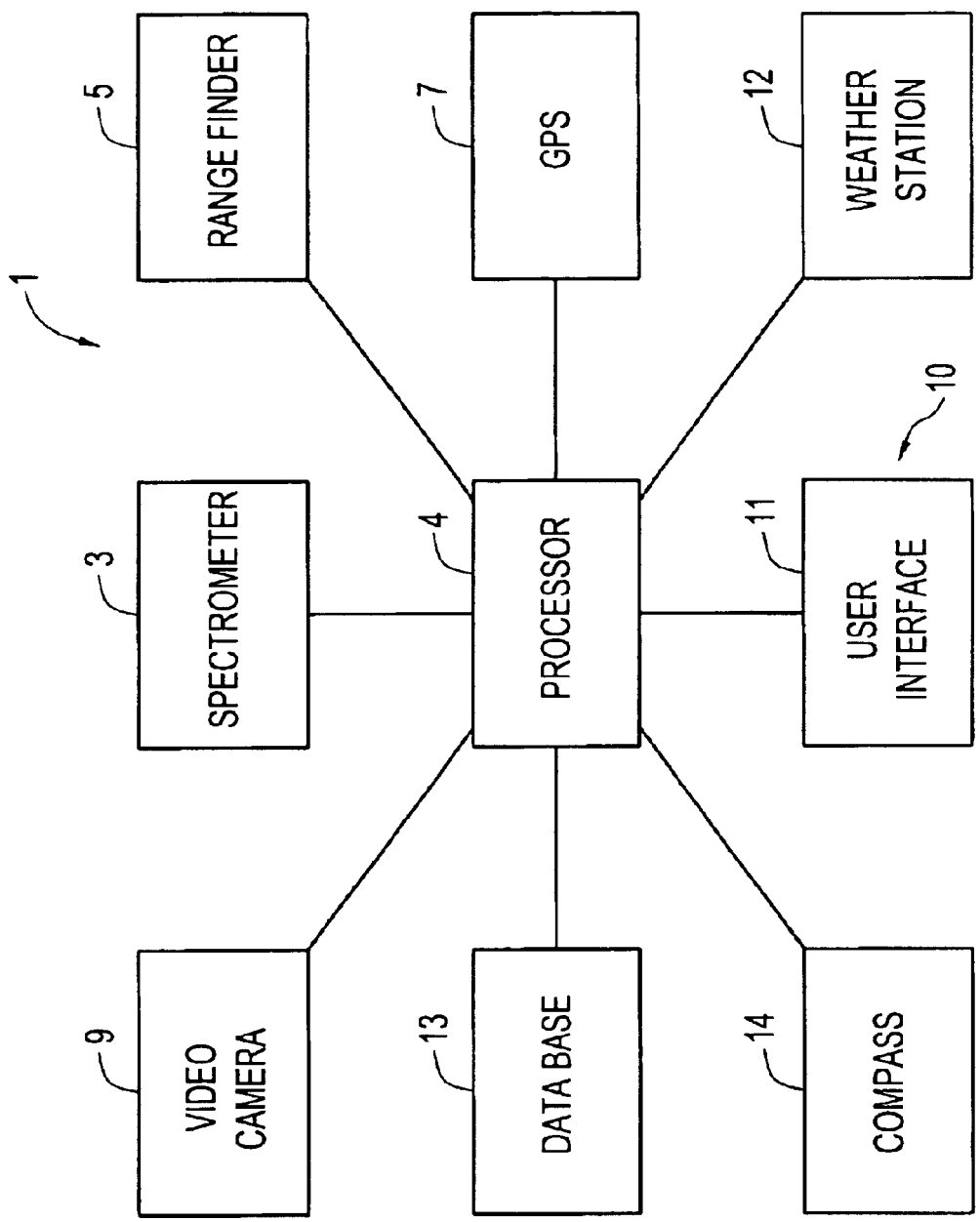
FIG. 4 is a conceptual hardware diagram for the system of the present invention.

To carry out both the spectral and non-spectral identification methods of the present invention, the invention employs a unique combination of hardware to form a system for remotely identifying compounds present in a chemical release. FIG. 4 is a block diagram illustrating the hardware used in the remote identification system of the present invention. Generally speaking, remote chemical identification system 1 will include a spectrometer 3, a location identifier 7, a range finder 5, a user interface 10, a computer processor 4, a weather station 12, a video camera 9 and a database 13 of chemical reference spectra. While not shown in FIG. 4, it will be understood that a spectral search engine will be run on processor 4. One example of such a spectral search engine is described below in reference to FIGS. 15–27. In a preferred embodiment, spectrometer 2 will consist of a passive infra-red spectrometer such as that sold under the tradename "Illuminator" by MIDAC Corporation of Costa Mesa, Calif. Location identifier 7 will be a conventional Global Positioning System (GPS) such as sold by the Trimble corporation of Sunnyvale, Calif. under the tradename "SVee8Plus". The range finder 5 will typically be a laser based ranger finder such as that sold under the tradename "ImpulseXL" by Laser Technology of Englewood, Calif. The video camera may be of any conventional type with the "VK-C77U" sold by Hitachi corporation being used in a preferred embodiment. The compass 14 can be any type providing an electronic signal output such as the HMR3000 sold by Honeywell corporation. The weather station is a device capable of measuring climatic conditions such as wind speed, ambient temperature, and humidity, one suitable example of which is the "1-Wire Weather Station" sold by Texas Weather Instruments of Dallas, Tex. User Interface 10 in one preferred embodiment comprises a conventional touch screen 11 and an alphanumeric keyboard. The processor 4 should be at least a 1 GHz processor and be installed with at least 512 MB of RAM and a large capacity memory such as a hard disk drive. In one preferred embodiment, the spectrometer 3, location identifier 7, range finder 5, user interface 10, computer processor 4, weather station 12, and video camera 9 will be organized into a single housing (not shown) with this housing normally being adapted for mounting on a vehicle for placement at a fixed site, or mounting on a support structure (e.g. a tripod) for standalone applications. The database 11 may exist on the hard disk drive or may be located remotely and accessed, for example, by a wireless data link or fiber optic link.

The database 13 will contain, among other information, a library of chemical reference spectra. As mentioned above, the reference spectrum of a chemical compound provides the absorbance of that compound at the particular wavelengths at which that compound absorbs or emits IR radiation. Databases of reference spectra are well known in the art and are available from companies such as Thermo Galactic of Salem, N.H. However, chemical compound identification based upon spectral data forms only one aspect of the present invention. In one preferred embodiment, the database will include not only chemical spectra data, but also a data associating observable properties with specific chemical compounds and/or data associating a location with specific chemical compounds. Nor is the term "database" limited to data on a single storage device. For example, the database could include a portion of the information on a local storage device (e.g. the hard drive) and a portion of the information located remotely (e.g. a remote server). Alternatively, the database could exist entirely on a storage device remote from the other components of the system.

This disclosure first details a method of identifying chemical compounds based upon certain properties, conditions or characteristics observed at the site of the chemical release. This method will normally be implemented in a computer system having a processor, a user interface executable software programs, and a database associating observable properties with specific chemical compounds. The processor and user interface may be of the type described above in reference to FIG. 4. The database will comprise a plurality of chemical compounds and for each compound associate a series of observable properties or characteristics. These properties normally pertain to compounds in a gaseous state, but could in some instances pertain to compounds in a solid or liquid state. In the particular embodiment described herein, these properties may include whether the compound produces a visible vapor, whether the vapor sinks or rises, the vapor's color, any smell associated with the compound, and any change in color and smell upon the exposure of the compound to water (hydrolysis). A further property that may be included in the data are what secondary compounds arise from the incomplete combustion of the compound in question ("products of incomplete combustion" or PICs). Which of these properties various compounds exhibit is well known in the art and may be found in references such as the Pocket Guide to Chemical Hazards published by the U.S. National Institute for Occupational Safety and Health (NIOSH), the Material Safety Data Sheet (MSDS) normally published by the manufacturer of the chemical, and the Chemical Hazards Response Information System (CHRIS) published by the United States Coast Guard, all three of which are incorporated by reference herein in their entirety. The database may also include information relating to the health hazards posed by various compounds and information on how to treat exposure to the compounds or how to best safely contain and handle the compounds, as well as general and specific procedures to follow for a chemical release incident. This latter information may be found in sources such as the Emergency Response Guide 2000 (ERG 2000) published by the U.S. Department of Transportation and the U.S. Fire Administration (USFA) Hazardous Material Guide for First Responders published by the U.S. Federal Emergency Management Administration (FEMA), both of which are incorporated by reference herein in their entirety. As an example, FIG. 6 shows a conceptual diagram of a database of chemical properties. As suggested, different compounds (represented as compounds A, B, C, etc.) will be associated with their respective chemical properties such as whether the compound produces a visible vapor (at atmospheric pressure), the density of that vapor relative to air, the color (if any) of the vapor, the smell (if any) of the compound, the molecular weight (MW), and the hydrolysis state (i.e. exposed to water) color, smell and density of the compound, if applicable. For illustration purposes, FIG. 6 is constructed as if compound "A" was ammonia and compound "B" hyperchlorous acid, with the applicable properties of each being presented. In the simplest example, the chemical properties database could take the form of a computer read look-up table. However, those skilled in the art will recognize many more sophisticated database structures. For example, in one preferred embodiment a computer would build a database schema within a case tool, such as Microsoft Visio, then create the database within a SQL relational database, such as Microsoft SQL Server that would allow for the unique relationship, cross reference, query and display of the information contained within all guides.

Figure 5:
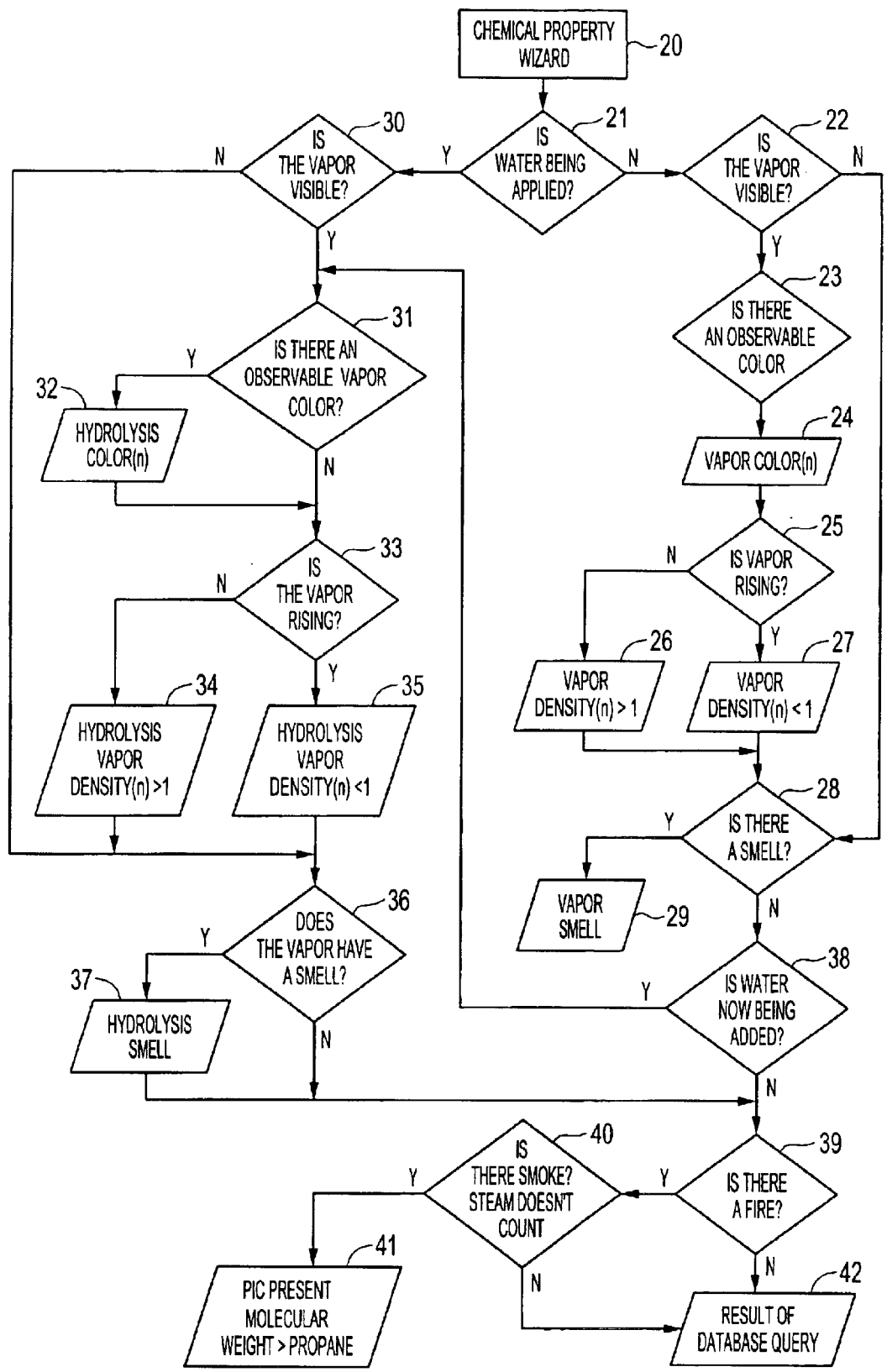
FIG. 5 is a flow chart for the Chemical Properties Wizard of the present invention.

FIG. 5 is a flow chart of the method for indicating the potential presence of a chemical compound or group of compounds based upon observable conditions at the site of the chemical release. When this method is implemented on a computer, it will typically take the form of a "Wizard" or program which seeks information from a user in a series of queries and provides a solution or feedback based on the information entered. This embodiment of the invention shown in FIG. 5 may be referred to herein as the "Chemical Property Wizard."

Beginning with step 20, the program will first identify for the user what Wizard routine is about to be executed. In step 21, the program first queries as to whether water is being applied to the chemical release (e.g. with a fire hose). If the response is affirmative, hydrolysis conditions may exist and the steps taken are described in steps 30–37 below. Assuming for the moment water is not being applied to the chemical release, the user is queried in step 22 whether vapor is visible when the user observes the chemical release. If yes, step 23 queries whether there is an observable color in the vapor. In the embodiment of FIG. 5, step 24 then presents the user with a choice of color bars on touch screen 11. As suggested above, the database will associate certain compounds with certain colors. Typically the program will present the user with ten to twenty color bars with the name of the color printed below the bar. It will be understood that more than one compound could be identified by the same color. However, the identification of a color does serve to narrow down the potential number of compounds likely to be present in the chemical release. Once a color is selected, the program moves to step 25 and queries the user as to whether the vapor is rising. If the vapor is rising, it is presumed in step 27 that the vapor density is less than 1 $mg/ms^3$ (the density of ambient air). If the vapor is sinking, it is presumed that the vapor density is less than 1 $mg/m^3$. Additionally, chemicals that have the same vapor density as air (1.0) tend to disperse uniformly into the surrounding air where contained and, when released into the open air, chemicals that are lighter than air will travel up and away from the ground. Step 28 next enquires if there is a smell associated with the chemical release. In a manner similar to that described in regards to colors, descriptions of all chemical odors named in the database will be presented to the user on touch screen 11 in step 29. For example, the USFA HazMat Guide, which describes the smell of various compounds, describes ammonia as having a "pungent odor" or hyperchlorous acid as having a "bleach-like" smell. After the user has indicated whether or not the odor of the released chemical matches with any of the odors listed on touch screen 11, the program will advance to step 38. Step 38 queries the user as to whether water is now being applied to the chemical release. If yes, a hydrolysis reaction may have occurred giving the chemical release a different color and different smell. The fact that the compound has altered color, smell or density upon hydrolysis may provide further evidence concerning the identity of the compound. It can be seen that step 30 may be reached by answering "yes" to the query in either step 38 or step 21. The affirmative answer in step 21 anticipates the situation where the system user first observes the chemical release with water already being applied. The affirmative answer in step 38 anticipates the situation where the release is first observed without the presence of water and water is later applied. Step 31 queries whether there is a new vapor color as a result of the hydrolysis. If yes, step 32 again displays to the user a selection of colors on touch screen 11 and allows the user to select one of the colors, before moving to step 33. Thereafter (or if there was no color change upon hydrolysis), step 33 queries whether the vapor is rising and steps 34 or 35 make a decision regarding vapor density as discussed above based upon whether or not the vapor is rising. Then steps 36 and 37 will make a new inquiry regarding the smell of the released compound in the hydrolysis state. Step 39 will then query whether there is a fire associated with the chemical release and whether there is accompanying smoke (step 40). If there is accompanying smoke (the user must distinguish between smoke from the fire and any steam from vaporizing water), step 41 will determine that the molecular weight of the substance burning is greater than the molecular weight of propane (i.e. 44). This conclusion is based on the premise that substances of greater molecular weight than propane will tend to produce visible smoke when they burn.

Once all queries have been answered, the program will return a listing of all chemical compounds for which the database has properties input by the user. In one preferred embodiment of the present invention, a compound will only be indicated present when all input properties match that compound. It should be understood that the program will not always return a suspected compound and often may return several compounds which meet the observed properties.

Another embodiment of the present invention relates to a database associating a location with specific chemical compounds. The physical location at issue will typically be an industrial plant or other facility which houses chemicals as part of its business operations. Information on what chemicals exist at what facilities may be obtained from Local Emergency Planning Commissions (LEPCs) and State Emergency Response Commissions (SERCs) or by other means entered into the database, for example, a fire departments pre-planning data. The Emergency Planning and Community Right to Know Act (EPCRA) has established that facilities storing, producing or using potentially hazardous chemicals must submit annually an emergency and hazardous chemical inventory form to LEPCs, SERCs and local first responders such as fire departments. Facilities provide this information in either a "Tier I" or "Tier II" form. Most States require the Tier II form and this provides basic facility identification information, employee contact information for both emergencies and non-emergencies, and information about chemicals stored or used at the facility. This information is publicly available and may be organized into an electronic database format. Tier I & II information normally identifies the location of a facility in terms of a street address and the address of the facility may be referred to as the "assigned map location" of the chemical compounds stored at that facility.

Figure 7:
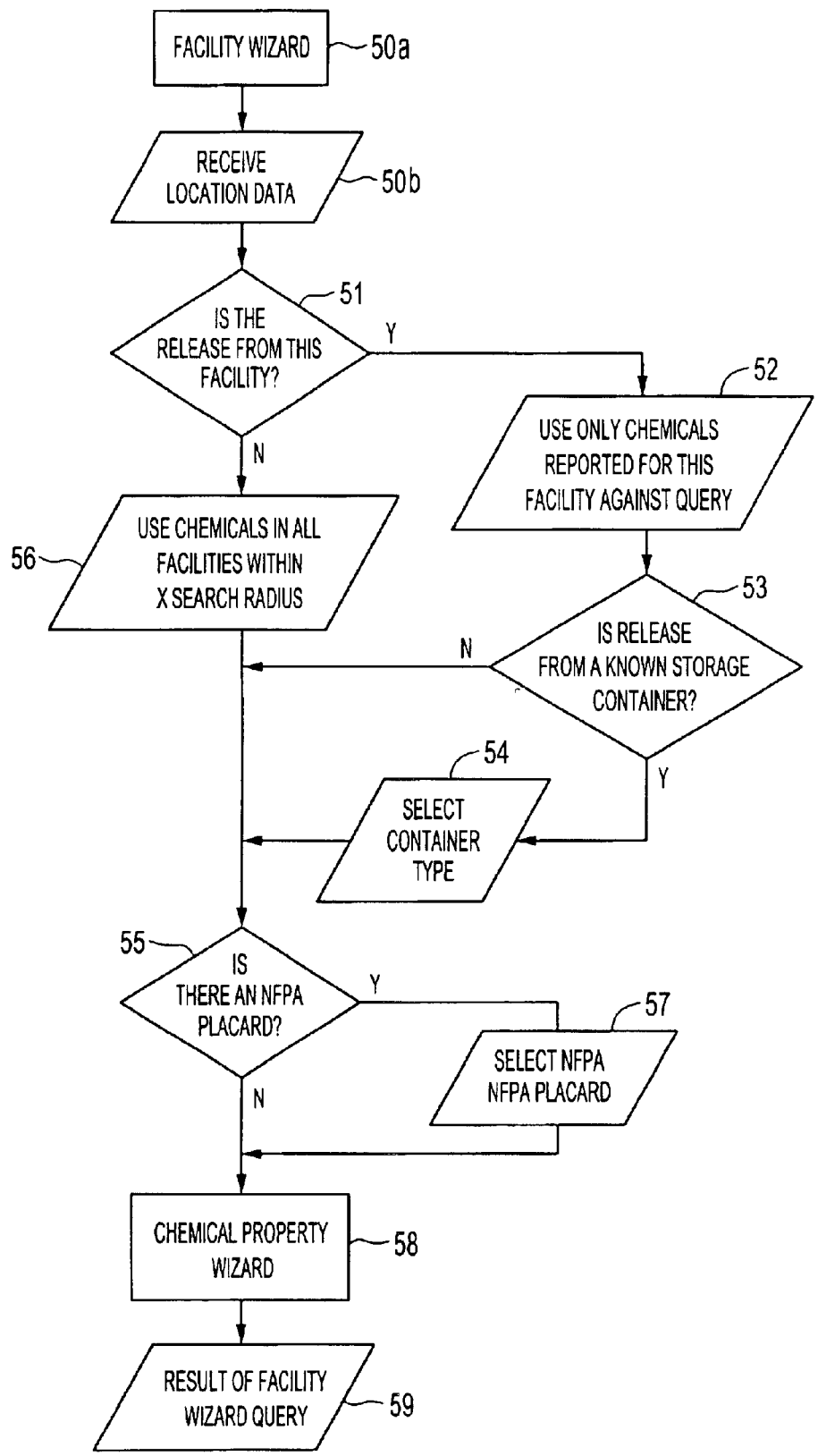
FIG. 7 is a flow chart for the Facility Wizard of the present invention.

FIG. 7 illustrates a flow chart for the method of correlating location data input by a user with a database having Tier I or II data. Normally this method will be implemented by way of computer software and will sometimes be referred to herein as the "Facility Wizard" program. Step 50*a* represents initiation of the Facility Wizard program. In step 50*b*, the program will receive an input representing the physical location of interest. When the Facility Wizard is operating in a hardware configuration such as seen in FIG. 4, the location input will be automatically provided by the Global Positioning System (GPS) unit 7, thus making the "system location" the location of the GPS device. GPS location data could be in the standard National Engineers and Mechanics Association (NEMA) GPS format which includes degrees and minutes latitude and longitude with the minutes being measure to a precision of six figures beyond the decimal point. However, there are other well known GPS message formats that will accomplish the same end. Since Tier I and II data normally provide facility location in terms of a street address, the Facility Wizard utilizes a conventional mapping program such as Microsoft Map-Point with an address geo-coding feature to associate the longitude/latitude data with the closest corresponding street address data.

Figure 8:
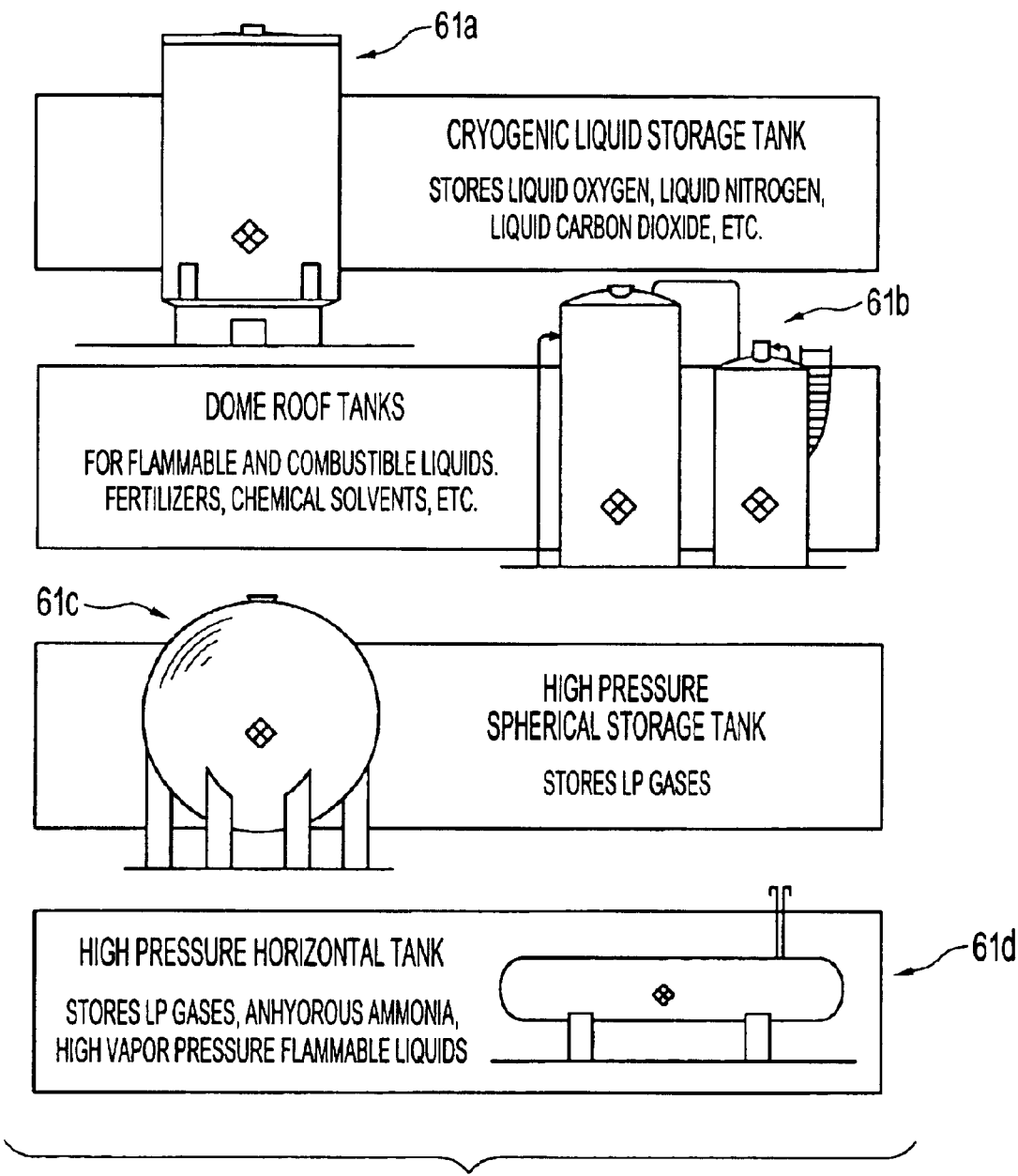
FIG. 8 is an example of container silhouettes utilized in the present invention.

The Facility Wizard next gives the facility name the Tier II data associates with the chosen location and queries the user in step 51 whether this is the facility in which the user believes the chemical release is located or from which the release is emanating. If the user responds in the negative, step 56 will automatically return a list of all chemicals reported in facilities within a given radius of the input location. In one embodiment, this radius has a default value of 0.5 miles, but the radius may be increased or decreased by user input. Alternatively, if the query in step 51 elicits a positive response, only the chemicals reported for the identified facility will be listed as suggested in step 52. Next, step 53 will query the user as to whether the release is from a known storage container. If the user can identify the container from which the release emanates, step 54 of the Facility Wizard will present the user with a selection of container silhouettes on touch screen 11. FIG. 8 illustrates a four examples of container silhouettes 61*a*–64*d* which could be presented to a user. The fact that a release is emanating from a particular container type does not precisely identify the compound being released, but it does limit the type or class of compounds which are likely to be stored in such a container. All information on storage containers and the types of products for which the containers are rated is publicly available from sources such as the United States Fire Administration (USFA) Hazmat Guide.

Figure 9:
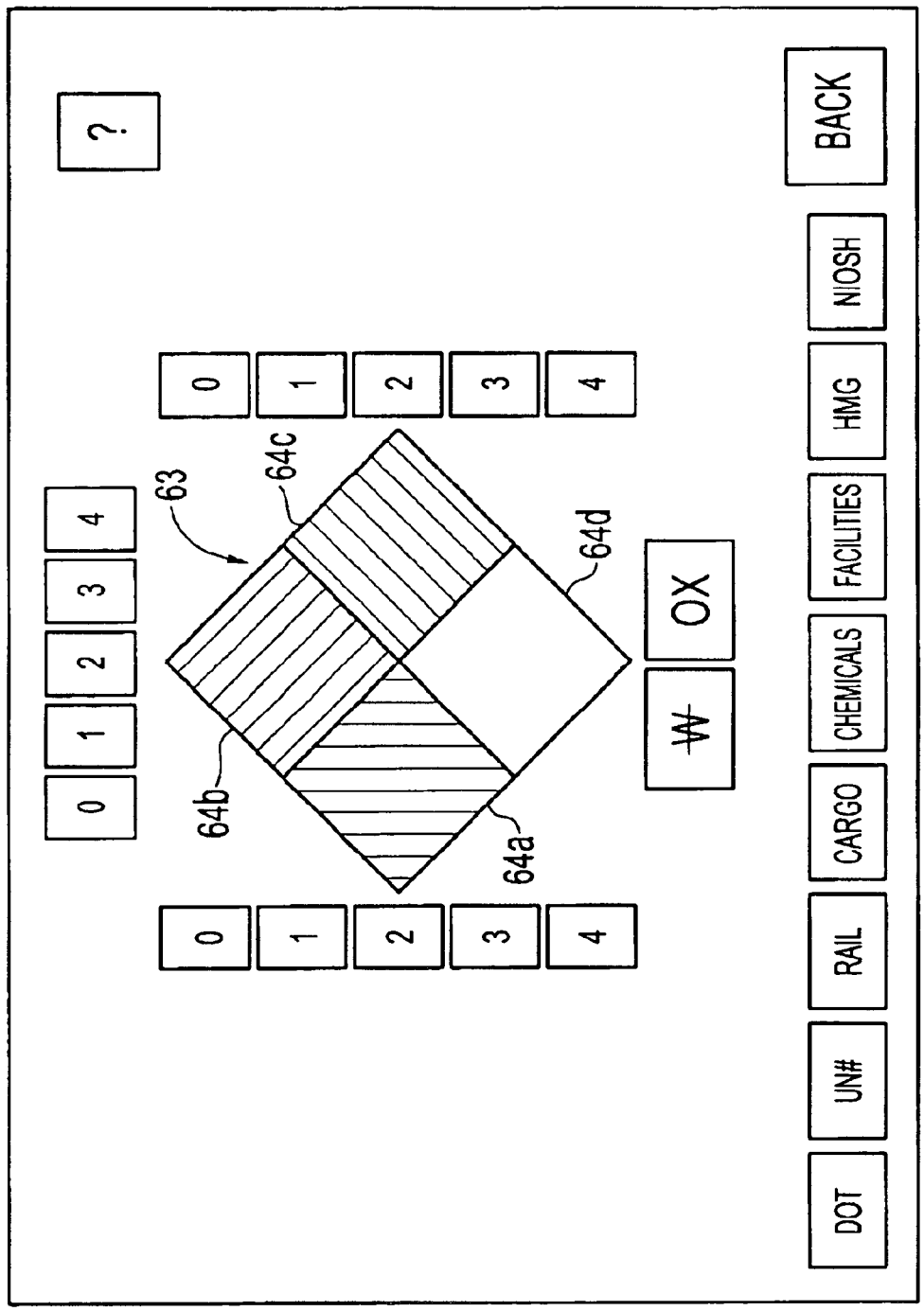
FIG. 9 is a screen-shot from a NFPA placard selection routine utilized in the present invention.

Regardless of whether the Facility Wizard branches to step 56 or step 54, the program will next query the user in step 55 whether there is an information placard such as a National Fire Protection Association (NFPA) placard as shown in the screen shot of FIG. 9. As is well known in the art, the NFPA placard 63 is divided into four diamond shaped fields represented as 64*a*–64*d*. Field 64*a* is blue (heath risk), field 64*b* is red (flammability), field 64*c* is yellow (reactivity), and field 64*d* is white (special concerns). Fields 64*a*–64*c* will also include a number from 0–4 in the field, where the numeral represents an increasing degree of each of the categories of health risk, flammability, or reactivity. Field 64*d* will have special alphabetical letter codes contained therein to indicate special concerns such as hydrolysis. Step 57 prompts the user to select a particular NFPA placard. In the embodiment shown in FIG. 9, this will entail the user reproducing on touch screen 11 the placard he or she is observing. This is done by touching the number or letters next to fields 64*a*–64*b* to reproduce the placard values observed at the site of the chemical release. As with the container silhouettes, the NFPA placards do not necessarily provide an exact compound, but there typically is a group of compounds which will correspond to a placard having a specific set of numbers.

In step 58, the Facility Wizard will initiate the Chemical Property Wizard program discussed above in reference to FIG. 5 and the Chemical Property Wizard will present the user with its set of queries and return any potential chemical compounds indicated based upon its decision process. In step 59, the results of the Facility Wizard steps 50–57 and the Chemical Property Wizard will be compared and chemical compounds common to both will be presented as the final results of the Facility Wizard.

Figure 10:
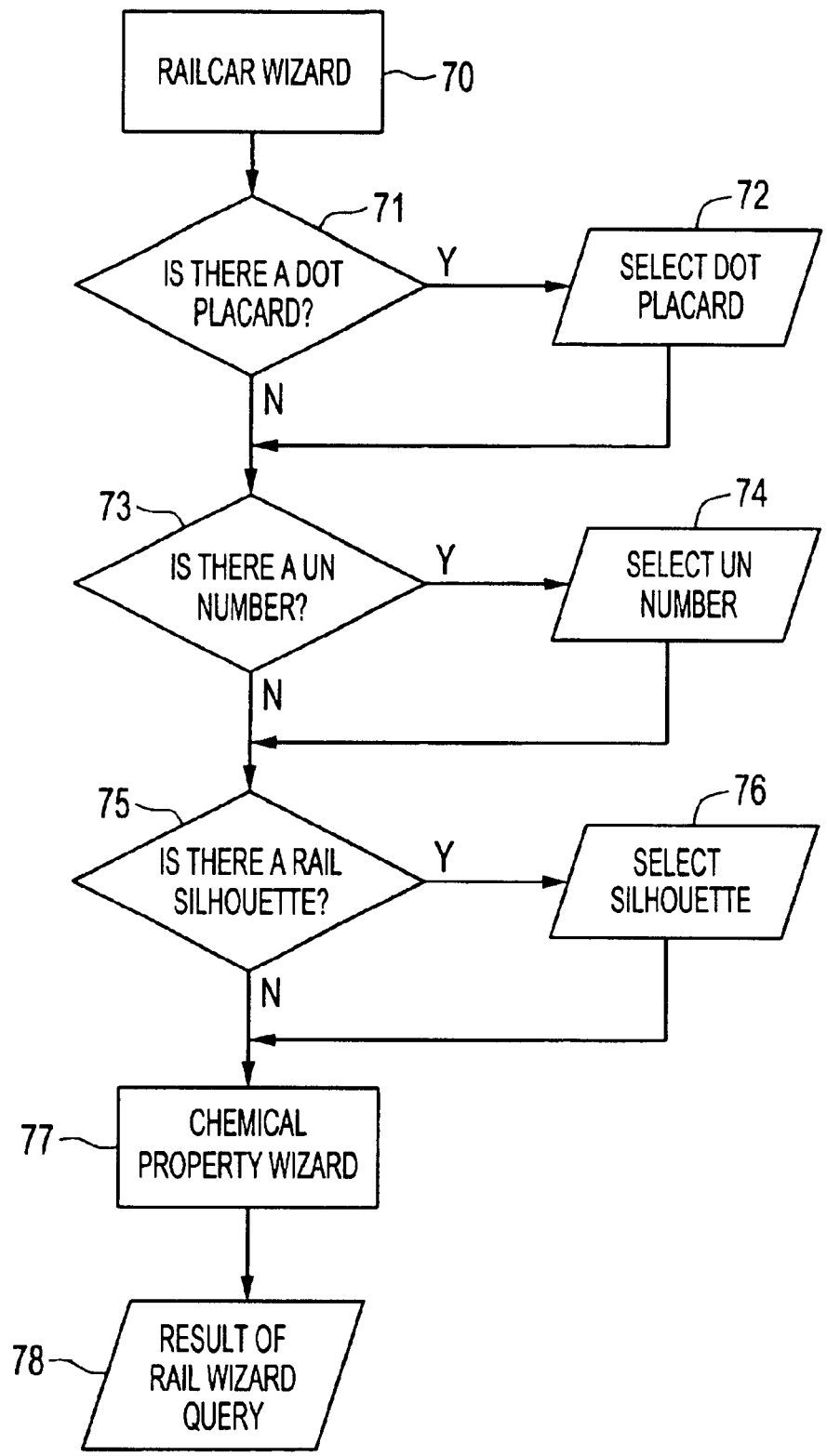
FIG. 10 is a flow chart of a Railcar Wizard of the present invention.
Figure 11:
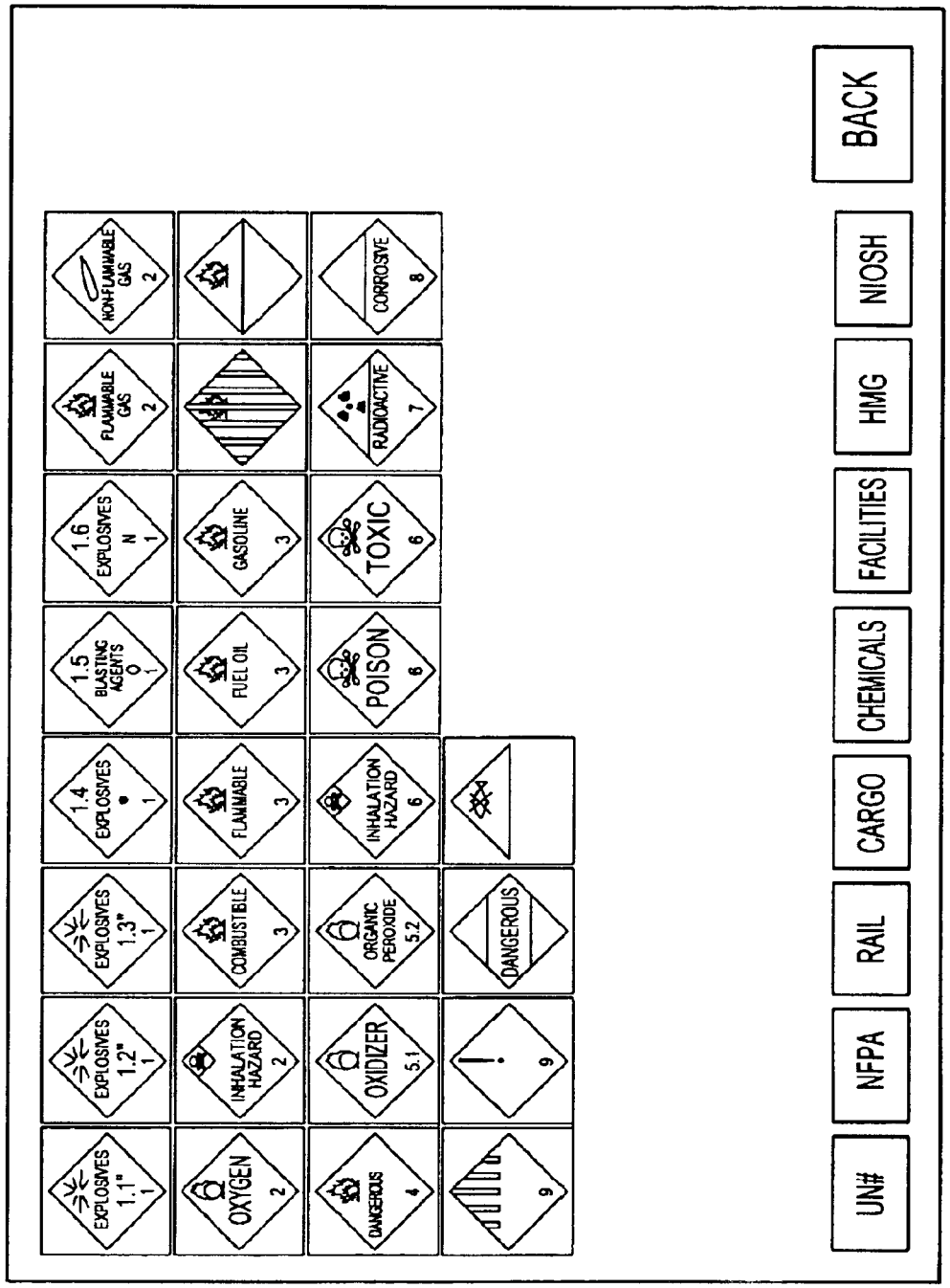
FIG. 11 is a screen-shot of a DOT placards selection routine utilized in the present invention.

Another embodiment of the present invention relates to a method (typically computer based) for identifying potential chemical compounds based on information observed on highway container trailers or railroad container cars. FIG. 10 illustrates a flow chart for what may be characterized as a "Railcar Wizard" for use when a chemical release is emanating from a railcar. It will be understood that while described in terms of a railroad tanker car, the procedure is equally applicable to highway container trailers and such is clearly contemplated by the present invention. Step 70 will initiate the program on touch screen 11 (see FIG. 4). In step 71, the user will be prompted to observe whether a U.S. Department of Transportation (DOT) placard exists on the railcar with which the chemical release is associated. FIG. 11 illustrates several typical DOT placards which may appear on touch screen 11 when the Railcar Wizard is in operation. Then the user will simply indicate the placard observed at the site by pressing the corresponding placard displayed on touch screen 11 as suggested in step 72. In some instances, the placard will specifically identify the compound in the container car (see for example the placards for oxygen and gasoline). However, in most cases, the DOT placard will only provide certain general properties (e.g. combustible, flammable, toxic, etc.) which could apply to several chemical compounds as in the case of NFPA placards discussed above. All compounds associated with the selected placard will be noted by the program as potential results of the Railcar Wizard.

Regardless of whether an applicable DOT placard is identified, the railcar wizard will next query the user as to whether there is an existing United Nations (UN) number. The UN number normally appears as a four digit number within a circle and may appear on DOT placards or a separate placard. The UN number is a unique number assigned to each chemical compound and can typically be found in any published hazardous materials guide. In one embodiment of the present invention, the user will use the touch screen to select the sequence of digits making up the UN number observed at the release site.

Figure 12:
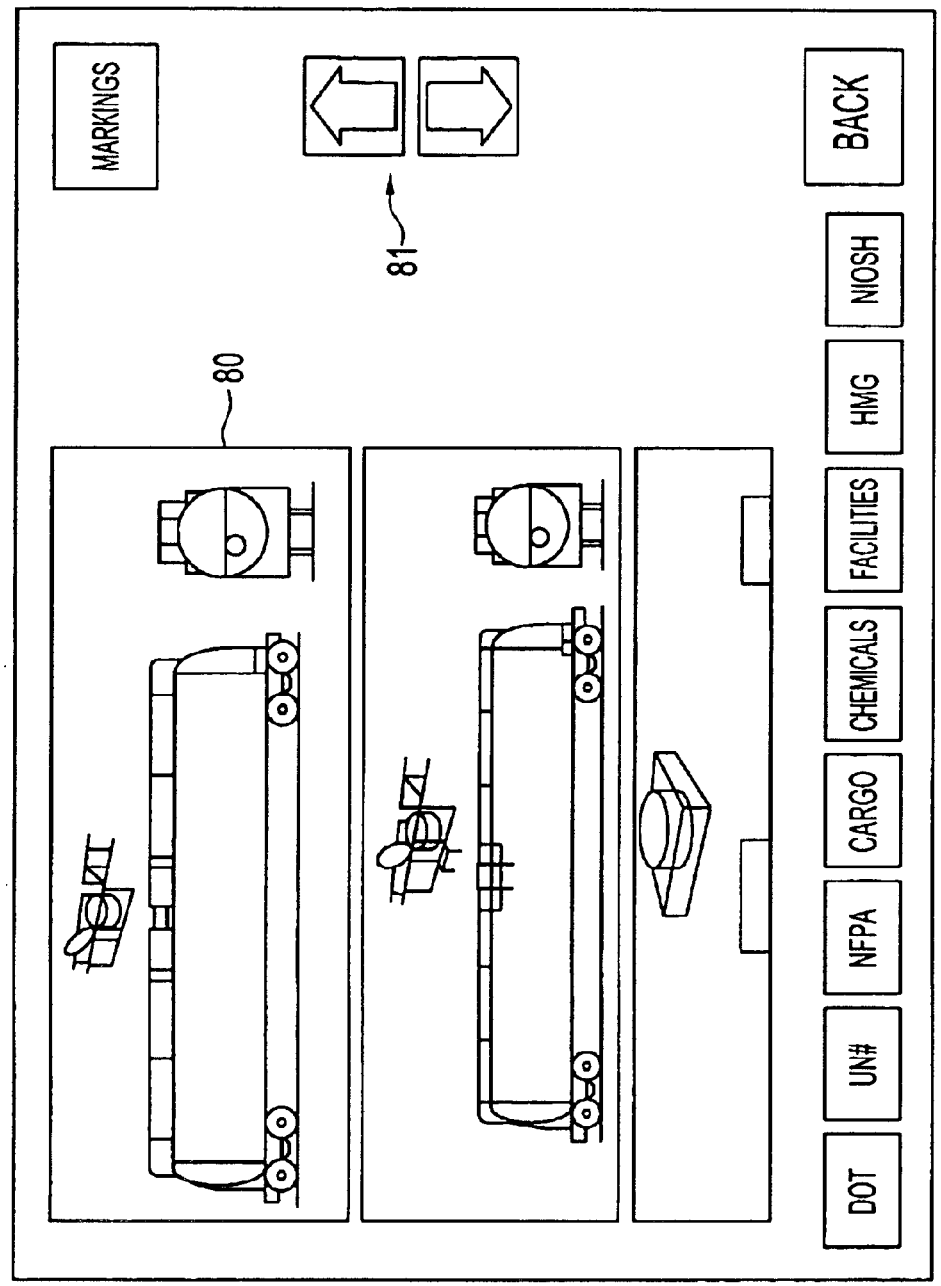
FIG. 12 is a screen-shot of a tank car silhouettes selection routine used in the present invention.

After inquiring concerning the UN number, the Railcar Wizard will next query the user in step 75 concerning whether there is a railcar silhouette in the database which matches the railcar associated with the release. The USFA Hazardous Materials Guide for First Responders includes a series of rail tank car silhouettes typically used in the railroad industry. The USFA Hazardous Materials Guide will indicate certain types of tank cars are designated for certain compounds. For example, the DOT 105J100W tank car is designated for ethylene oxide, liquefied petroleum gas and liquefied hydrocarbon gas, while the DOT 105J200W tank car is designated for sulfur dioxide, vinyl chloride, and liquefied petroleum gas. FIG. 12 shows a screen shot illustrating how the Railcar Wizard will direct the user to select the proper railcar which is observed at the incident location. Using up/down selection arrows 81, the user will scroll through different silhouettes in the database and compare the silhouettes 80 to the observed railcar. The user will simply touch the appropriate railcar to indicate that this is the railcar observed at the scene.

After a silhouette is selected in step 76, the Railcar Wizard will call up in step 77 the Chemical Property Wizard discussed above and it will present the user with its set of queries and will return any potential chemical compounds indicated based on its decision process. In step 78, the results of steps 70–76 and the Chemical Property Wizard will be compared and chemical compounds common to both will be presented as the final results of the Railcar Wizard. Although the UN number, when properly updated on the container, is the most accurate identifier of the compound, there is no way to assure the UN number has in fact been updated. Therefore, a compound is only identified by the programs when the compound identified by the UN number also corresponds to the chemical or chemicals identified by the other indicators (silhouettes, DOT/NFPA placards, the chemical property wizard).

2. Spectral Identification of Compounds

Figure 13:
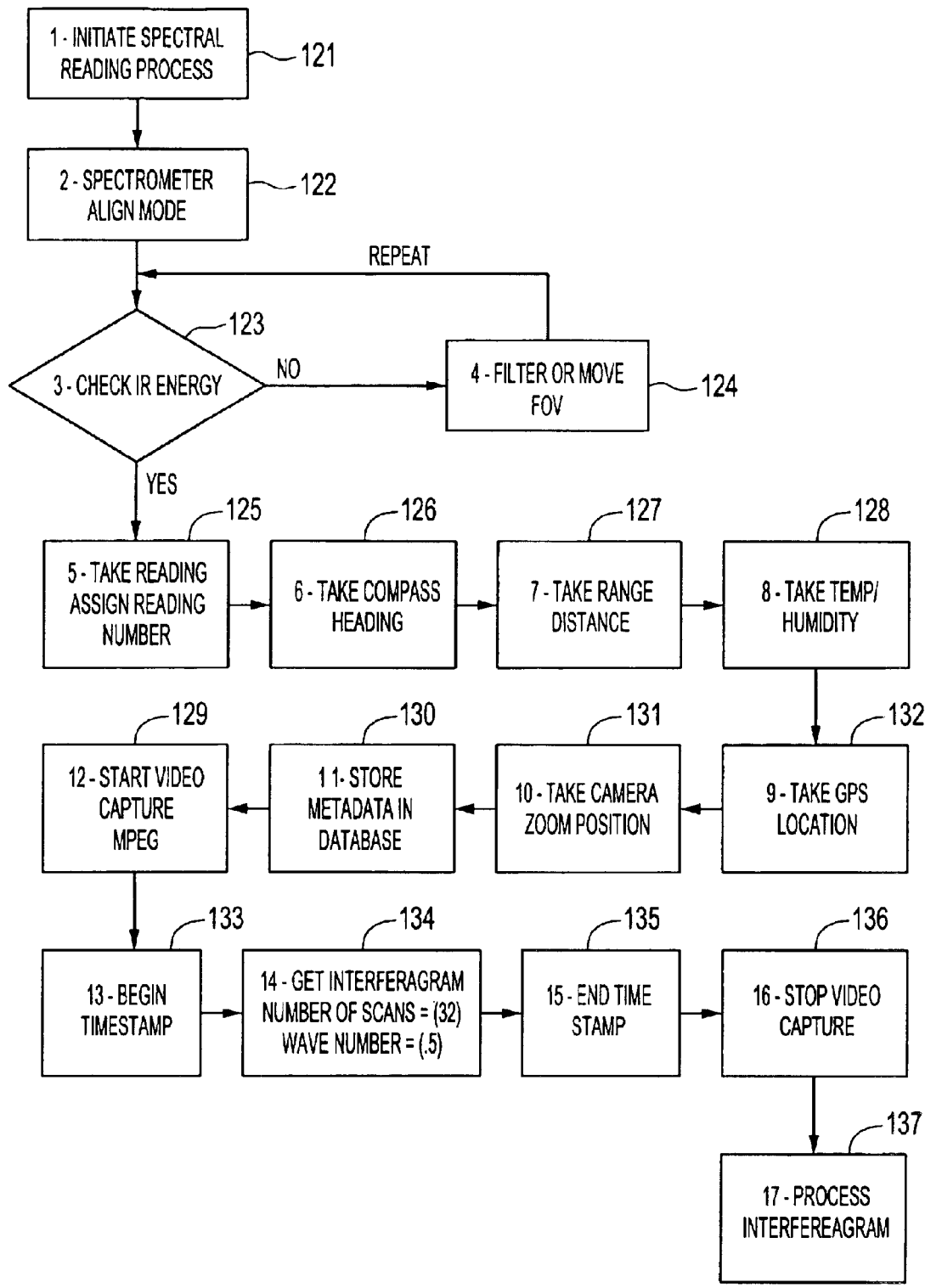
FIG. 13 is a flow chart illustrating the steps in taking a spectral reading.

Another major aspect of the present invention is the use of spectral analysis to remotely identify unknown compounds in a chemical release. As discussed above, one of the key parameters in performing reliable remote spectral analysis is an accurate background spectrum. The present invention provides a novel and advantageous manner of producing an accurate background spectrum. However, as a preliminary process to determining the background spectrum, FIG. 13 illustrates how the present invention performs several initial steps as it takes its first spectral readings. The first step 121 initiates the spectral reading process by calling step 122 involving an "alignment mode" procedure which is executed by existing software in the spectrometer. These steps are briefly discussed in reference to FIG. 14. In this mode, the spectrometer will take a single interferometer scan and transform the scan (via FET with triangular apodization) to a sample single beam spectrum ($SB^S_i$) over the frequency range of $v=650$ cm$^{-1}$ to $4200$ cm$^{-1}$ (step 141).

Next, the system estimates of the total incident infrared power in the signal by measuring the difference between the minimum and maximum values (peak-to-peak value) of the interferogram (step 142). The magnitude of the IR signal power may be represented by any conventional numeric or graphical user interface. If the signal power is greater than the recommended power range of the spectrometer, the user will place an IR filter across the spectrometer lens and take another reading of the signal power. If the signal power is less than the recommended range, the user will attempt further readings from different locations, which may result in the transmission of more IR energy to the spectrometer. If no angle of view provides sufficient signal power, then no spectral reading is possible under existing conditions.

Once the system confirms there is sufficient signal power, the system perform several further steps to provide additional data. As suggested in FIG. 13, for each spectral reading the system will assign the reading a specific identification number (step 125), take a compass heading (step 126), take a range measurement to the backdrop object (step 127), take a temperature and humidity reading (step 128), take a GPS reading (step 132), take a camera zoom position (step 131), store metadata from the video capture (step 130), start video capture which may be stored in a conventional JPEG format (step 129), begin video timestamp (step 133), make a predetermined number of scans at a pre-selected wave interval to construct an interferogram (step 134), end the time stamp (step 135), stop the video capture (step 136), and then process the interferogram (step 137). In a preferred embodiment, thirty-two scans will be made with the interferometer, at a 0.5 wave number interval, in order to construct a composite interferogram. The operation of the interferometer and the processing of the interferogram is well known in the art and need not be described further herein.

Figure 14:
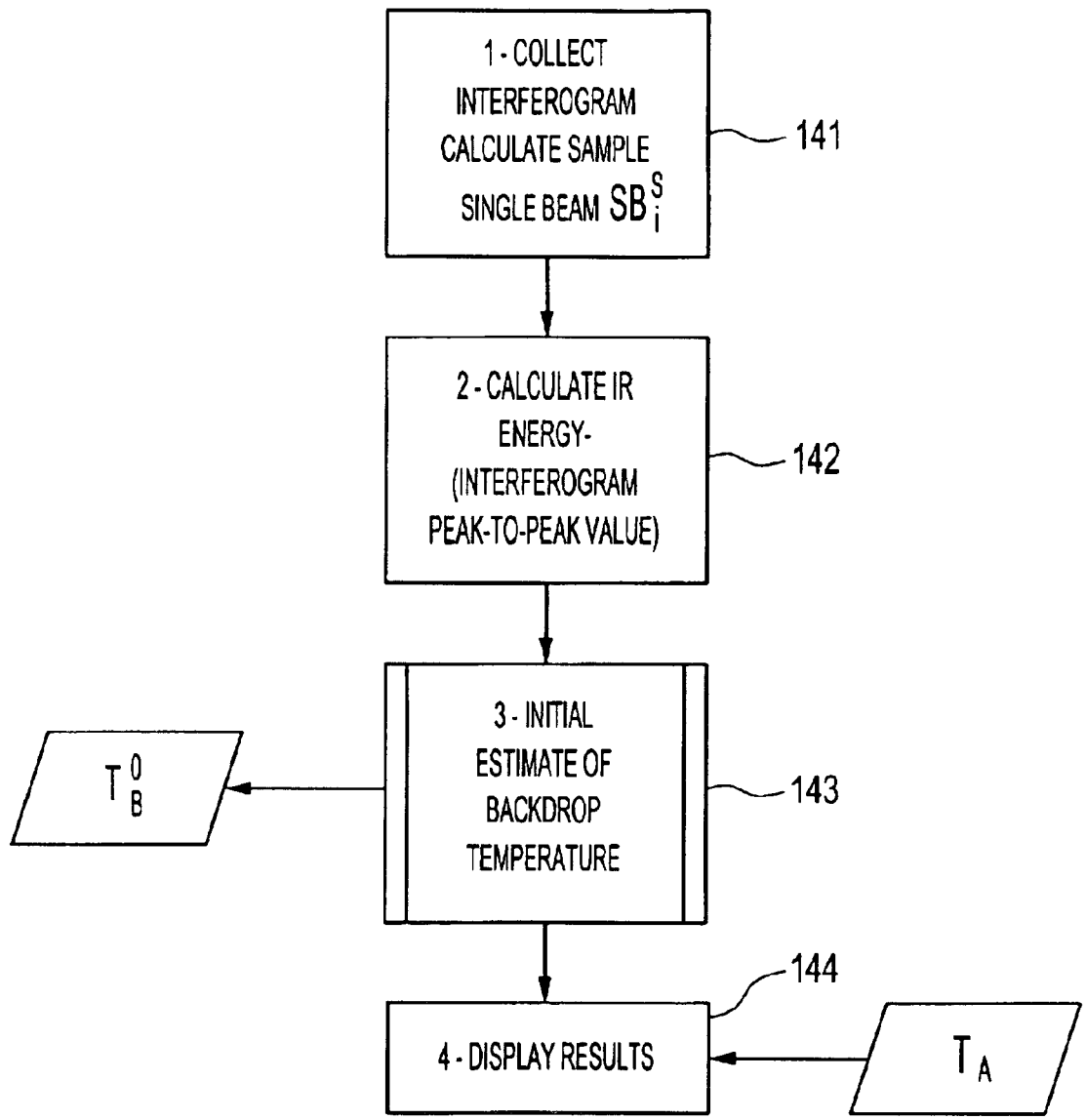
FIG. 14 is a flow chart illustrating the steps in aligning the spectrometer.
Figure 15:
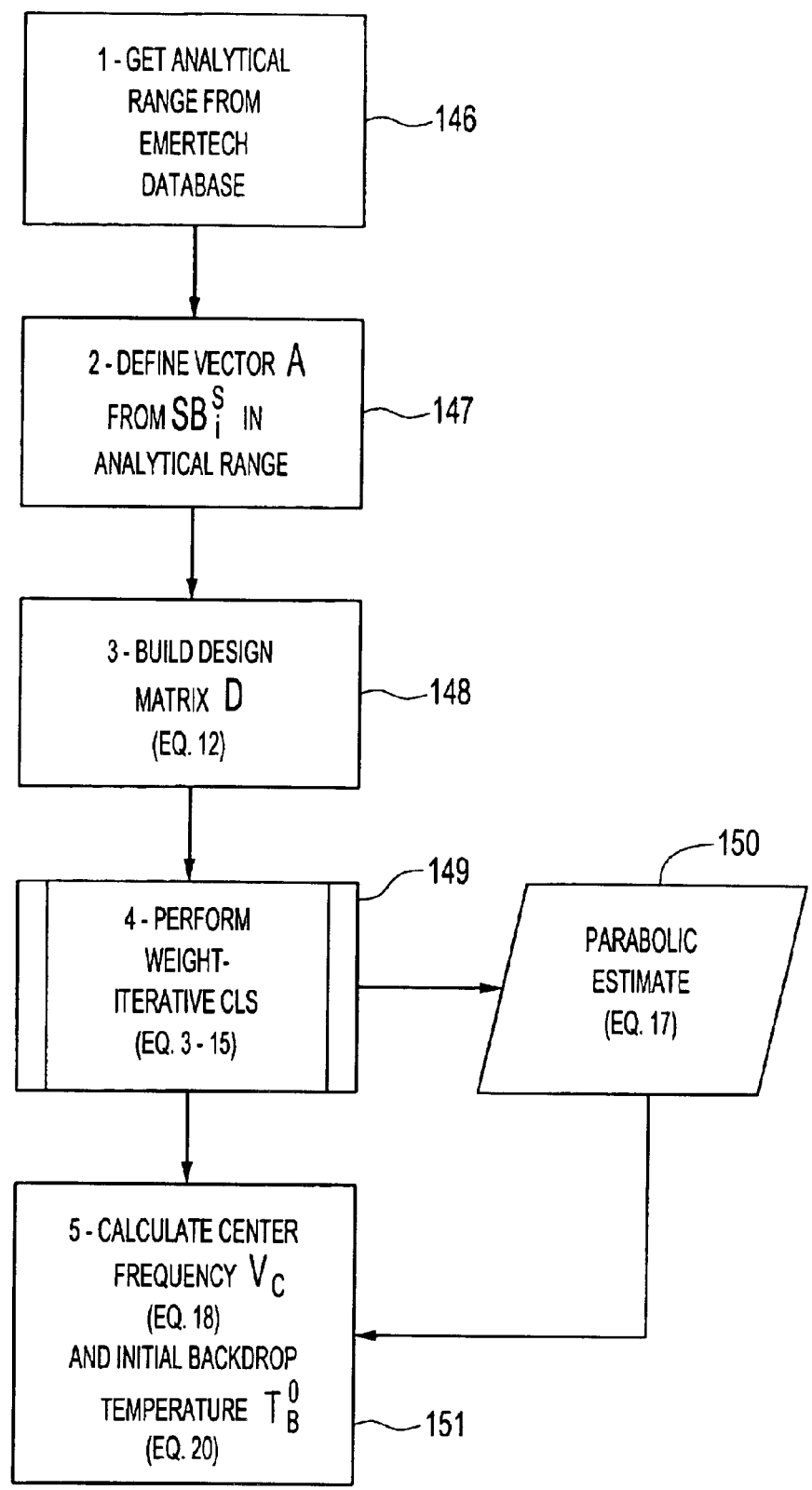
FIG. 15 is a flow chart illustrating the steps in estimating an initial backdrop temperature.

One of the steps shown in FIG. 14 (step 143) is making an initial estimate of the Background Temperature as described in FIG. 15. Before exploring the steps in FIG. 15, it is important to understand that in order to make this estimate, the system will utilize a database of known sample single beam spectra of various gas mixtures with known gas and backdrop temperatures.

Figure 19:
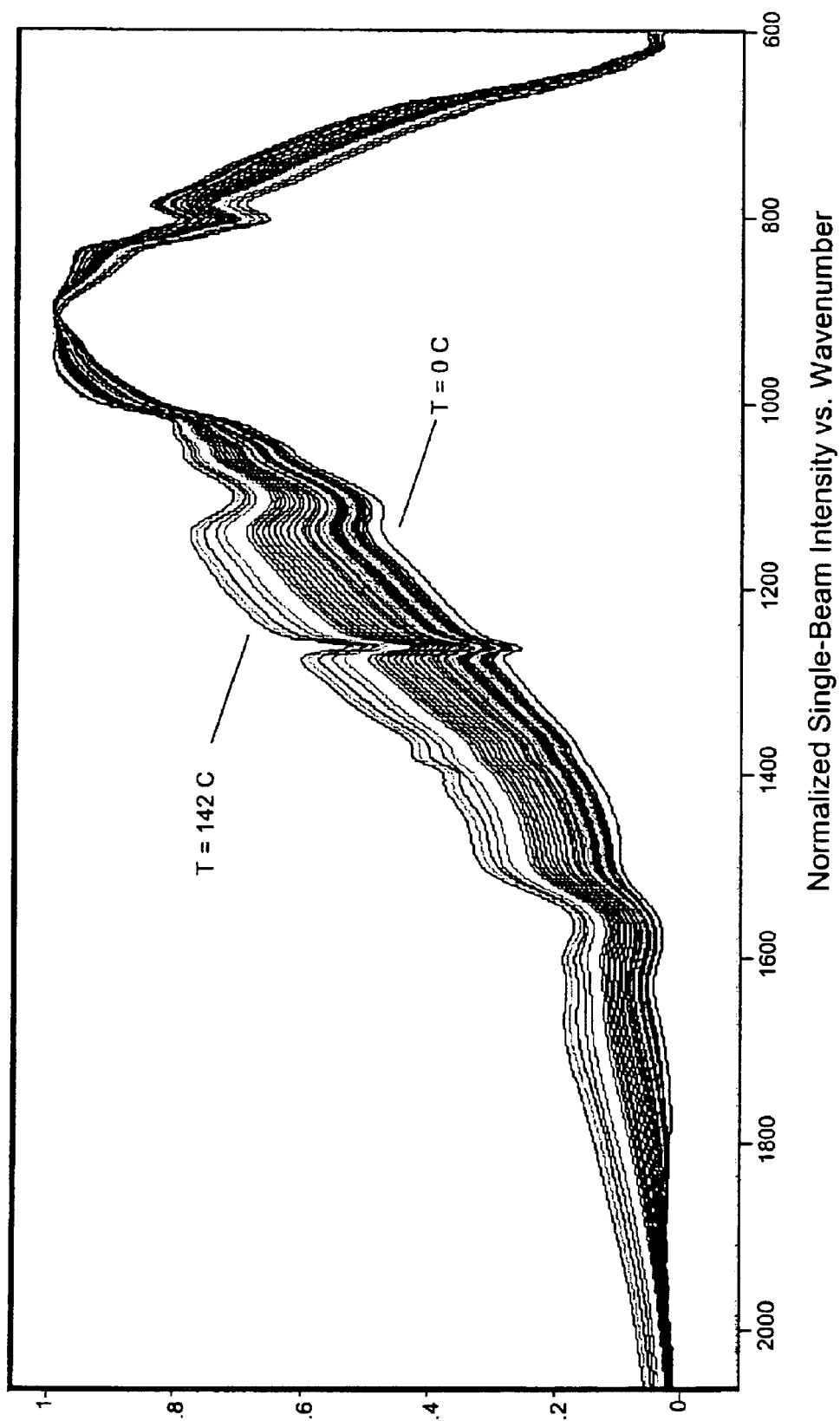
FIG. 19 illustrate a series of black body temperature curves.

In a preferred embodiment, forty-two single-beam backdrop spectra are used in estimating the sample background spectrum. These forty-two spectra represent the backdrop temperatures between 0.0 and 142° C., and are illustrated in FIG. 19; they were recorded using a Model 340 black body radiation source, manufactured by Mikron Infrared, Inc. of Oakland, N.J.

Another experimental procedure used to generate absorption spectra includes a heated, single-pass gas sample cell (with 10 centimeter absorption path length) and a solid, gray, 25 cm diameter "hot plate." K-type thermocouples attached to the surfaces of the hot plate and the absorption cell provided measurements of the temperatures of both the sample gas ($T_S$) and the backdrop ($T_B$). The spectra forming the set are recorded with the hot plate filling the field of view of the spectrometer and the gas cell positioned between the spectrometer and backdrop. These absorption spectra are used to generate the temperature contrast $\Delta T=T_A-T^0{}_B$ discussed below in Equations 18 through 20.

Figure 20:
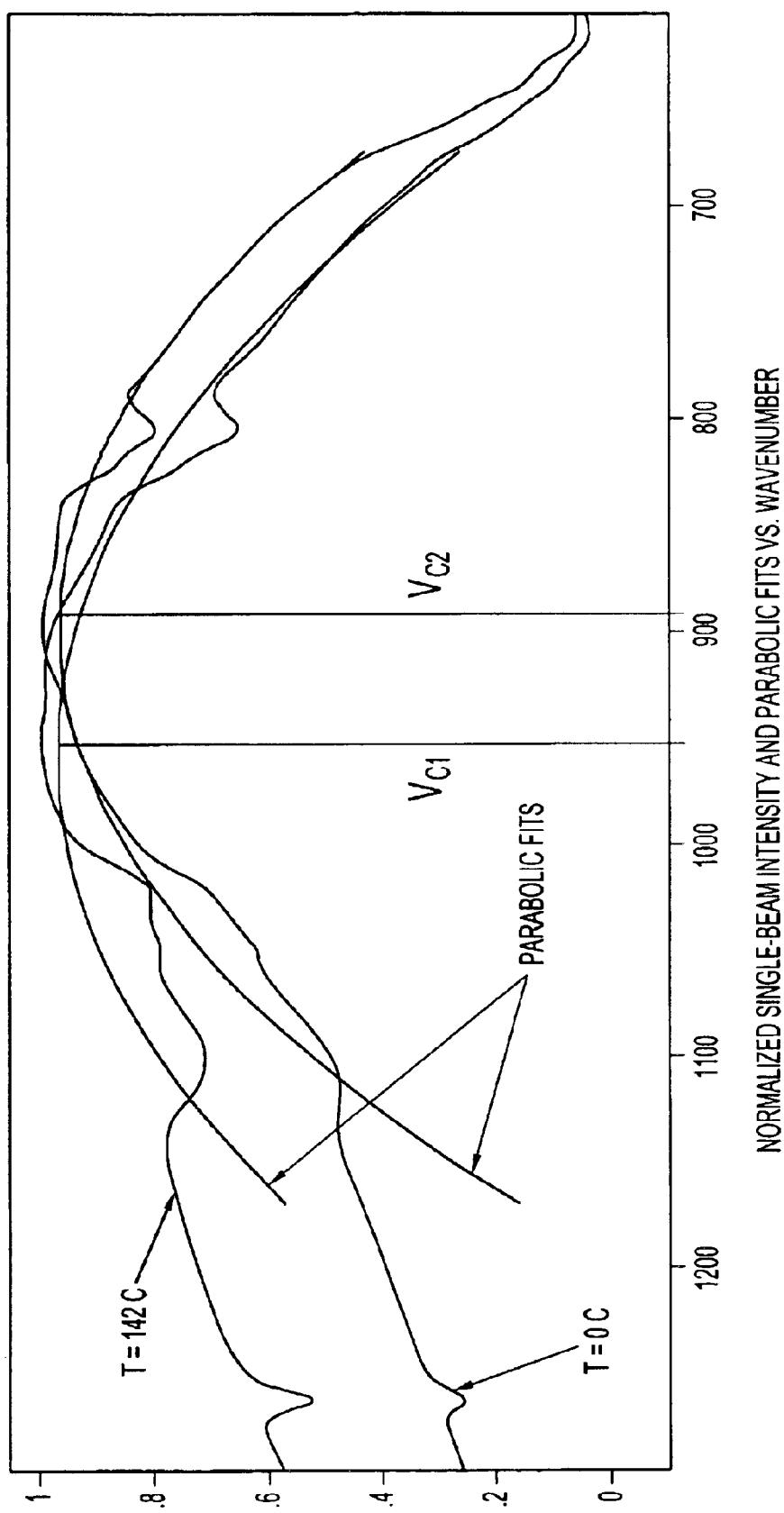
FIG. 20 illustrates parabolic fits to two black body temperature curves.

After the initial absorption spectra are generated, these spectra are modified by removing the gas-phase absorption features over a number (~200) of small frequency ranges (largely corresponding to H2O and CO2) and replacing these absorption features with cubic spline approximations to the relatively smooth, underlying emission spectrum of the backdrop. The spectra are also scaled to set their maximum values to unity. FIGS. 19 and 20 illustrate the resulting background reference set over the wavenumber region 650 to 1400 cm$^{-1}$. While FIG. 19 illustrates the entire set of backdrop spectra, for clarity, FIG. 20 shows only the spectra representing the minimum and maximum temperatures of the reference backdrop spectral set (0° and 142° C.).

Figure 21:
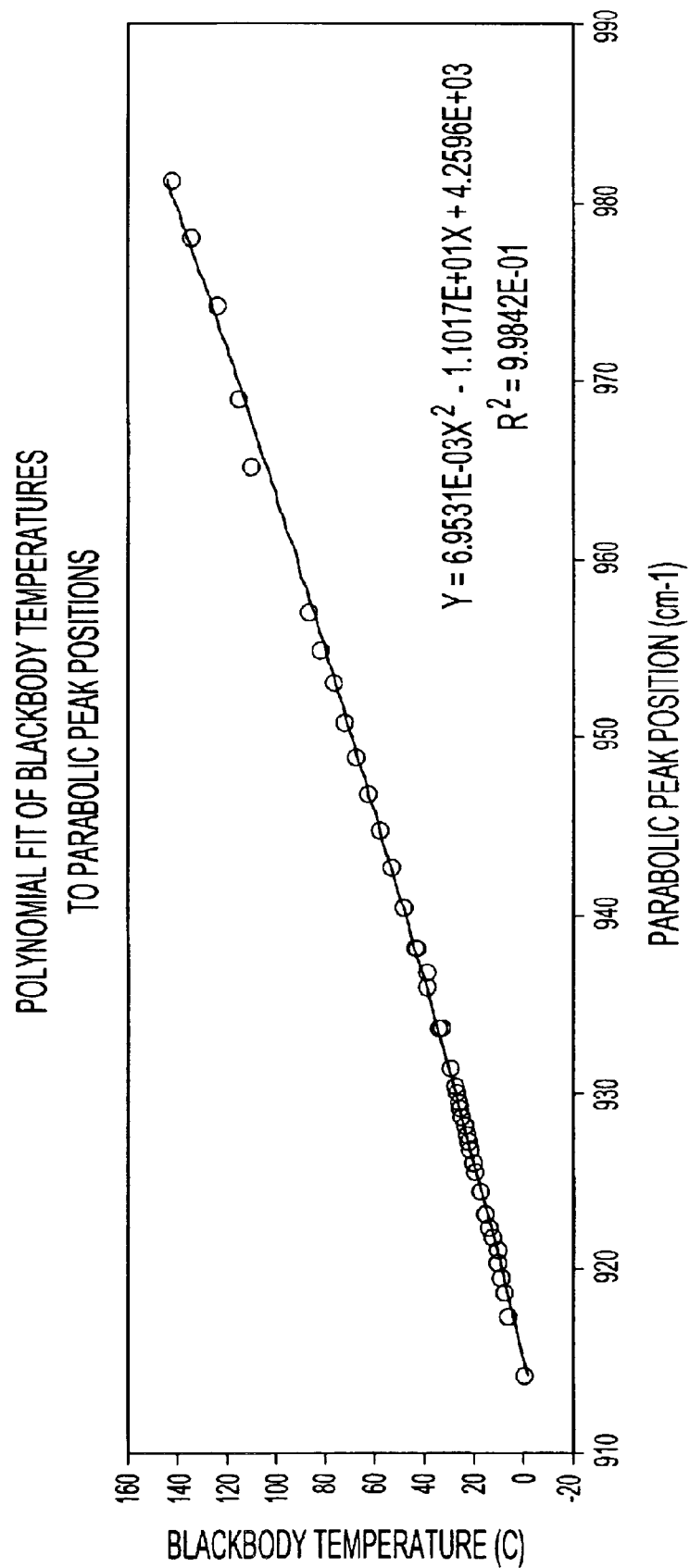
FIG. 21 illustrates a curve of parabolic peak positions to blackbody temperatures.

As illustrated in FIG. 20, a parabolic curve is shown fitted to each of these spectra (0° and 142° C.) and the maximum height or parabolic center of these parabolas are represented by $Vc_1$ and $Vc_2$. When numerous single beam spectra over a given temperature range (e.g. 0° and 142° C.) are generated (see FIG. 19), the parabolic centers of these single beam spectra may be estimated and the relationship representing backdrop temperature vs. parabolic center may be plotted as seen in FIG. 21. Using this relationship, it can be seen how given the estimated parabolic center of a sample spectrum an estimated temperature may be obtained by reading the point on the temperature axis corresponding to the parabolic center.

Now returning to FIG. 15, to implement this process as suggested by that figure, the system first obtains an analytical range from the spectrometer (step 146). The database contains the parameters between $v_A$ and $v_B$, which in one common embodiment may be defined as $v_A$=650 cm$^{-1}$ and $v_B$=1100 cm$^{-1}$. All the spectral information used in the described embodiment exists in standard disk files of a format developed by Thermo Galactic, Inc. of Salem, N.H. and referred to as the "SPC" format. The disk files consist of several blocks of header information followed by an ordered list of the spectral y-values representing either absorbance or infrared intensity, depending on the spectral data type. The header information contains, among other data, the frequency of the first y-data point (FFP), the frequency of the last y-data point (FLP) and the number of points in the file (NPTS). The x-axis values associated with the y-data are not stored in the file, but are calculated as needed from the positions of the data in the list, FFP, FLP, and NPTS. For instance, the frequency associated with the 13$^{th}$ y-value in the file is equal to $$FFP+(13-1)\left(\frac{FFP-FLP}{NPTS-1}\right).$$

All the spectral files used by the described embodiment have the same values of FFP, FLP, and NPTS, so the SPC file format lends itself easily to the construction of the columns in the design matrix D. From the upper frequency of the desired analytical range and the header information, it is possible to calculate the position of the corresponding y-value in the disk file list. This value is read from the disk file and placed in the first row of the design matrix column. Subsequent y-values (down to that datum corresponding to the lower frequency of the analytical range) are simply read sequentially from the disk file and placed sequentially in lower row positions of the same column of D.

The system will then define the components necessary for implementation of the matrix represented by equation 2. For example, Vector A is defined from $SB^S{}_i$ in the above determined analytical range (step 147 in FIG. 15). The vector components are the sample single beam values over the analytical range: $A_i=(SB)^S{}_i$ from $v_i=v_A$ to $v_B$. Then the system will build the Design Matrix D as suggested in step 148 in FIG. 15. The columns of D consist of constants, the values $v_i$, and the values $(v_i)^2$ to provide a matrix such as:

$$D=\begin{pmatrix} 1 & v_1 & (v_1)^2 \\ 1 & v_1 & (v_2)^2 \\ . & . & . \\ 1 & v_N & (v_N)^2 \end{pmatrix} \qquad \text{Eq. (12)}$$

The design matrix of Equation 12 represents a parabolic estimate of the sample single-beam spectrum over the frequency range $v_1$ to $v_N$; in current applications, $v_1$=650 (cm$^{-1}$) and $v_N$=1100 cm$^{-1}$. When the elements of the row vector A are set equal to those of the sample single-beam spectra over this frequency range and the initial (k=0) P matrix is set to the identity matrix I, Equation 9 yields estimates of the parameters $\bar{X}_L^k$ (L=0, 1, 2, ... N) where the estimated parabola is given by:

$$y_i=\bar{X}_0^k+\bar{X}_1^k v_i+\bar{X}_2^k v_i^2 \qquad \text{Eq. (13)}$$

and k denotes a "weight interative" CLS ("WICLS") iteration number.

The WICLS (step 149 in FIG. 15) is a novel CLS analysis performed by the present invention in order to obtain a more accurate estimated parabola (step 150) than would be obtained with the prior art CLS method. The WICLS technique employs iterative adjustments in the weight matrix P (Equation 5) on the basis of the residual V (Equation 7). In many cases, the change in the weighted sum of squared residuals $V^2$ (Equation 8) in successive iterations eventually drops below a predetermined positive value, signaling an end to the iterative process. This technique results in the effective rejection from the CLS analysis that subset of the measured data A (Equation 2) that is not well described by the linear model embodied in the design matrix D (Equation 3). As used in the present invention, the WICLS estimates $\bar{X}_j$ and their associated MSD values $\bar{\Delta}_j$ (Equations 9 and 11) are generally superior to those provided by standard CLS analyses.

Figure 16:
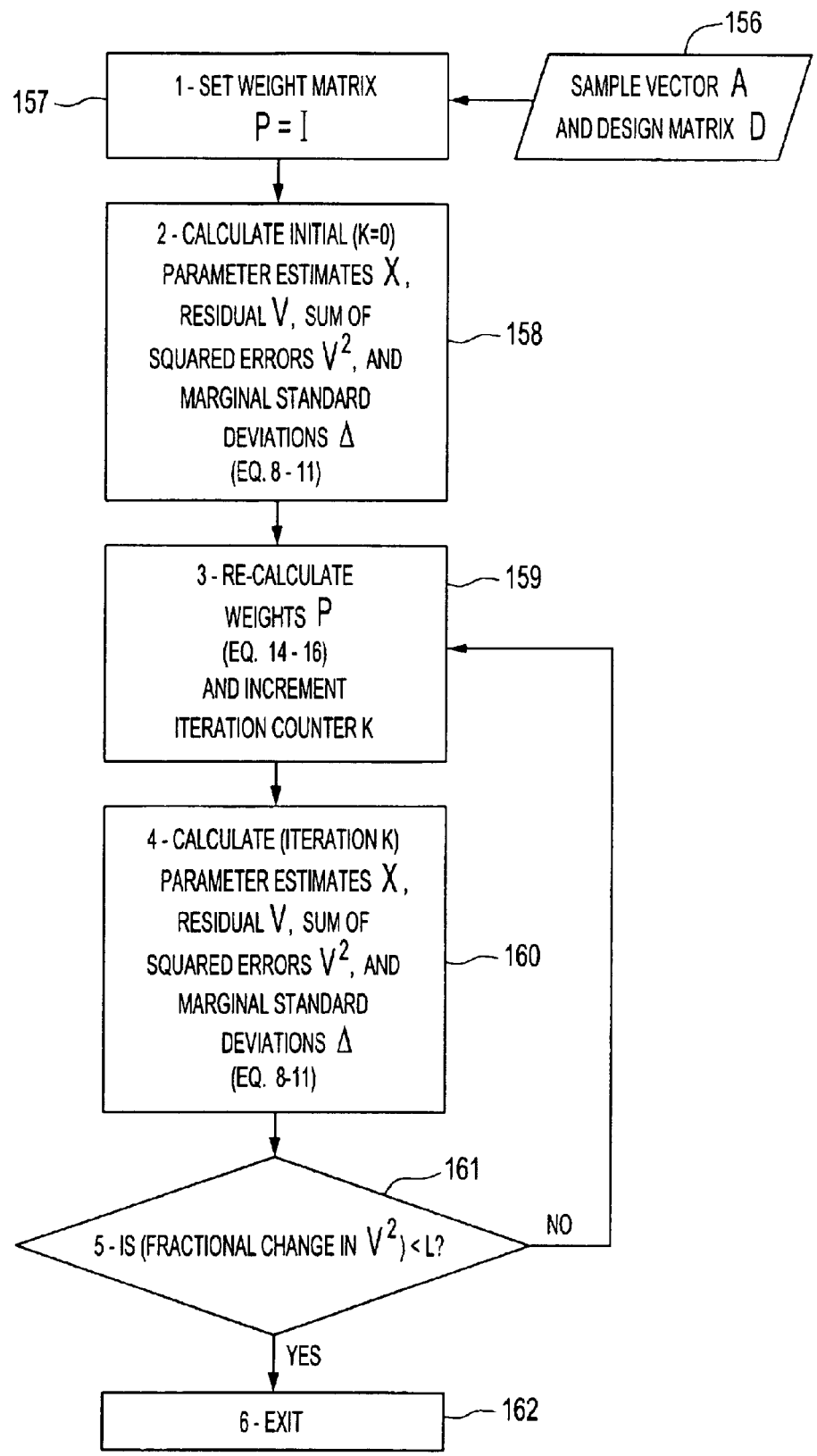
FIG. 16 is a flow chart illustrating the steps in weight interative CLS.

FIG. 16 illustrates the steps performed in implementing the WICLS technique. The matrices A and D are sampled in step 156. Prior to the first iteration in a WICLS analysis the weight matrix P is set equal to the identity matrix I (step 157), that is, all the data involved in the analysis are accorded equal weight. Next in step 158, the initial (k=0) Parameter Estimates $\bar{X}_j$, Residual V, Sum of Squared errors $V^2$, and Marginal Standard Deviations $\bar{\Delta}_j$ are calculated as disclosed above (See Equations 8–11). In step 159, the weights P are calculated and the iteration counter k incremented. Based on the residuals of the previous iteration, the weights are redefined according to the equations:

$$\xi_i^k=(1/V_i)^2 \qquad \text{Eq. (14)}$$

and their mean $$\bar{\xi}^k=\frac{1}{N}\sum_i \xi_i^k \qquad \text{Eq. (15)}$$

where the superscript k>0 denotes the iteration number. The weights $P_{ij}^{k+1}$ for the next $(k+1)^{th}$ iteration are determined from the (non-linear) relations $$P_{ii}^{k+1} = \begin{cases} \bar{\xi}^k & \text{if } \xi_i^k > \alpha \bar{\xi}^k \\ \text{or} \\ \xi_i^k & \text{if } \xi_i^k \leq \alpha \bar{\xi}^k \end{cases} \qquad \text{Eq. (16)}$$

and $$P_{ij}^{k+1} = 0 \text{ for } i \neq j \qquad \text{Eq. (16)}$$

where $\alpha \geq 0$ is an adjustable parameter determined experimentally for each WICLS application. In a preferred embodiment of the present invention, the value $\alpha = 1$. Employing the latest weights matrix P, the Parameter Estimates $\bar{X}_j$, Residual V, Sum of Squared errors $V^2$, and Marginal Standard Deviations $\bar{\Delta}_j$ are recalculated in step 160, again using Equations 8–11. In many cases, repeated iterations using Equations 12 through 16 forces convergence of the values $(\bar{X}_j)^k$, $(\bar{\Delta}_j)^k$, and $(V^2)^k$, where, again, the superscript k>0 denotes the iteration number. In such cases, the values of $(V^2)^k$ for subsequent values of k obey $$\text{abs}\left\{\frac{(V^2)^{k+1} - (V^2)^k}{(V^2)^{k+1}}\right\} < L \qquad \text{Eq. (17)}$$

When the condition expressed in Equation 17 is met (step 161), the values $(\bar{X}_j)^{k+1}$ and $(\bar{\Delta}_j)^{k+1}$ (and all other associated estimates) are taken as the values of the WICLS analysis. In a preferred embodiment, the value $L \approx 0.01$.

Application of the WICLS procedure described in Equations 12 through 17 will provide values for the $X_0^k, X_1^k, X_2^k$ from parabolas described in Equation 13. A final estimated center frequency $\nu_C$ for the parabola of interest (step 151) may be calculated as:

$$\nu_C = -\frac{\bar{X}_1^k}{2\bar{X}_2^k} \qquad \text{Eq. (18)}$$

As discussed above, the plot of the WICLS estimates of $\nu_C$ versus the known backdrop temperature seen in FIG. 21 will provide the basis for estimating backdrop temperature. A polynomial regression to the experimental data represented in FIG. 21 results in a functional estimate of the form:

$$y = a_0 + a_1 \nu_C + a_2 \nu_C^2 + a_3 \nu_C^3 + a_4 \nu_C^4 \qquad \text{Eq. (19)}$$

When the procedures described in Equations 16 through 19 are applied to a sample single beam spectrum of unknown backdrop temperature, they yield an estimate $\nu_C^S$ of the center frequency of that spectrum. The initial estimated backdrop temperature $T_B^0$ of that spectrum is given by $$T_B^0 = a_0 + a_1(\nu_C^S) + a_2(\nu_C^S)^2 + a_3(\nu_C^S)^3 + a_4(\nu_C^S)^4 \qquad \text{Eq. (20)}$$

The system displays a numerical or graphical representation of the backdrop temperature. This allows the system to present rapidly updated graphical outputs of IR energy and the temperature contrast $\Delta T = T_A - T_B^0$ (see Equations 18–20 and FIG. 28).

Once the system has determined the initial estimate of the backdrop temperature (step 176 in FIG. 18), it will proceed to construct a background spectrum. The initial estimate of the backdrop temperature, $T_B^0$, is used to select a "reference background single beam (SB) pair" which are the two background spectra which represent the closest spectrum above $T_B^0$ and the closest spectrum below $T_B^0$ (step 178).

For purposes of illustration, take the bottom most spectrum in FIG. 19, (0° C.) and take the adjacent spectrum (6.8° C.). If $T_B^0$ were between 0° C. and 6.8° C., these two spectra would be a reference background SB pair.

The estimated background SB spectrum will be generated by fitting the sample SB spectrum to the reference background SB pair by way the WICLS method described above (step 179). Denoting the intensity value of the reference background SB pair at the frequency $\nu_i$ as $S_i^1$ and $S_i^2$, a design matrix is formulated over the frequency range $\nu_1$ to $\nu_N$ as $$D = \begin{pmatrix} S_1^1 & S_1^2 \\ S_2^1 & S_2^2 \\ \cdot & \cdot \\ S_N^1 & S_N^2 \end{pmatrix} \qquad \text{Eq. (21)}$$

While the corresponding values of the sample single-beam spectra over the frequency range $\nu_1$ to $\nu_N$ are used as the input row vector A (see equation 2). As noted above, current applications employ the values $\nu_1 = 650$ cm$^{-1}$ and $\nu_N = 100$ cm$^{-1}$. Application of the WICLS procedure described in Equations 12 through 17 results in two estimates $\bar{X}_1$ and $\bar{X}_2$; the estimated background SB spectrum $SB_i^B$ is given by $$SB_i^B = \bar{X}_1 S_i^1 + \bar{X}_2 S_i^2 \qquad \text{Eq. (22)}$$

Figure 17:
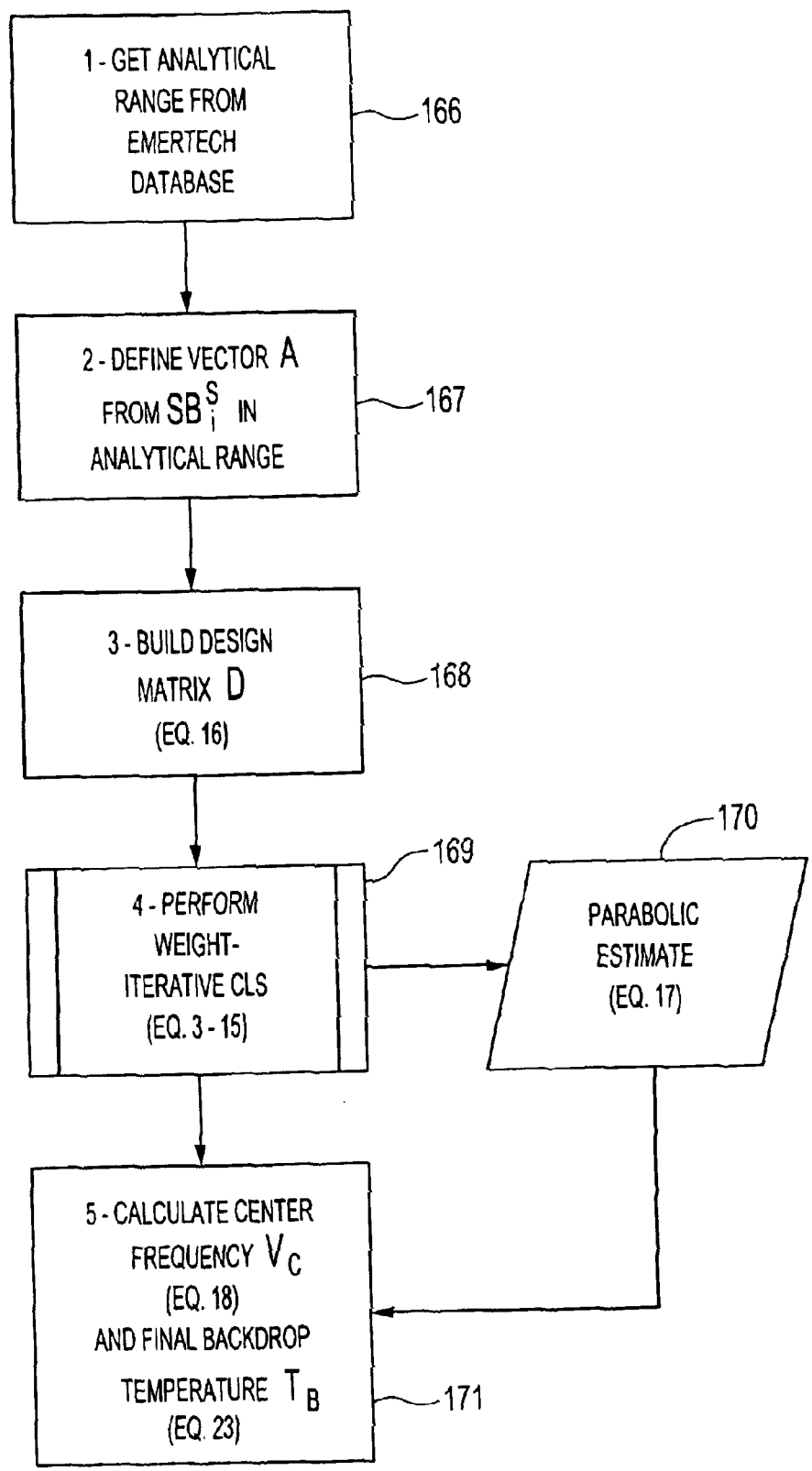
FIG. 17 is a flow chart illustrating the steps in estimating a final backdrop temperature.
Figure 18:
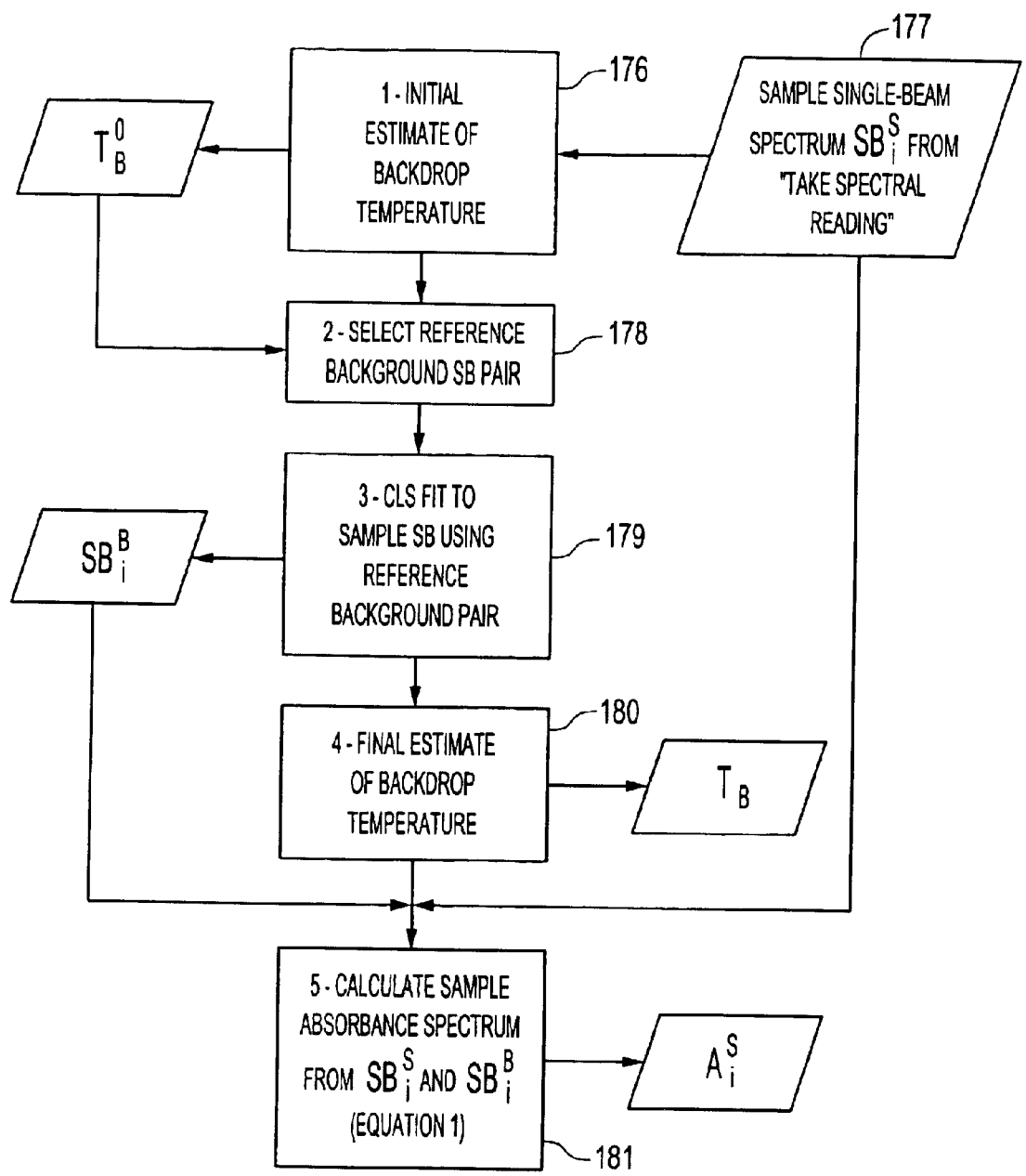
FIG. 18 is a flow chart illustrating the steps in generating a background and absorbance spectrum.

FIG. 17, step 171 provides that a final estimate of the Backdrop Temperature ($T_B$) is ultimately made by the system. The above described method of determining initial backdrop temperature, $T_B^0$, (equations 12 through 20) is employed except that the row vector A is set equal to the estimated background SB spectrum $SB_i^B$ (Equation 22), rather than the sample SB spectra as shown in FIG. 19. The final estimate of the backdrop temperature $T_B$ (step 180, FIG. 18) is given by Equation 23, which is analogous to Equation 20:

$$T_B = a_0 + a_1(\nu_C^S) + a_2(\nu_C^S)^2 + a_3(\nu_C^S)^3 + a_4(\nu_C^S)^4 \qquad \text{Eq. (23)}$$

Once the estimated background SB spectrum $SB_i^B$ is has been determined, the sample SB absorbance spectrum $SB_i^S$ may be calculated (FIG. 18, step 181) as is well known in the art using equation 1.

Once this sample absorbance spectrum is obtained, the present invention will begin the process of identifying which spectra for individual compounds are present in the absorbance spectrum. The system first uses a variety of methods to initially identify a set of compounds which appear to be represented in the sample spectrum. Then the system utilizes a second method to determine with increased certainty whether the compounds identified in the first search are actually represented in the reference spectrum.

Initial Identification of Compounds:

One method the present invention shall employ in making an initial identification of compounds which appear to be represented in the sample spectrum will be to compare the sample spectrum to the known absorbance spectrum for various compounds. The absorbance spectrum for many compounds is known and available from sources such as Thermo Galactic of Salem, N.H. As mentioned above, the spectral information provided by Thermo Galactic is compiled in standard disk files in a format developed by Thermo Galactic and referred to as the "SPC" format. The construction of the design Matrix D is the same as described above.

Figure 22:
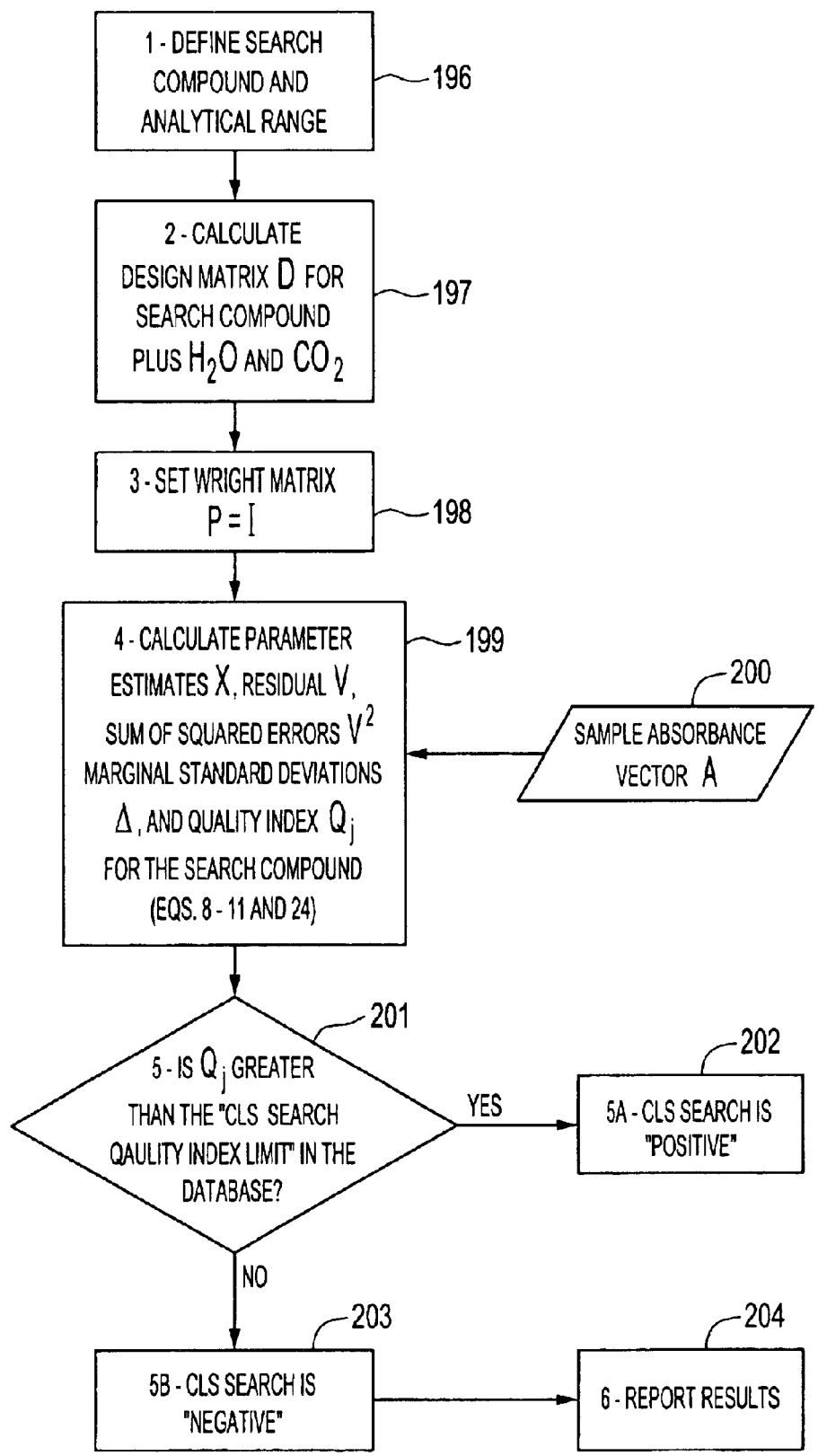
FIG. 22 is a flow chart illustrating the steps in a CLS search of the present invention.
Figure 23A:
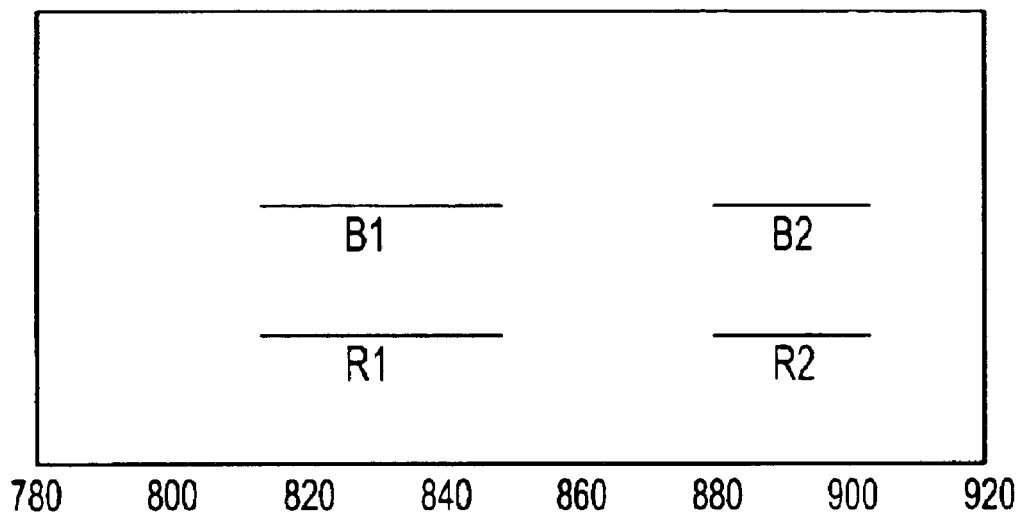
FIGS. 23a and 23b are analytical range representations.

With a database which associates a compound with a known spectrum or multiple known spectra (hereinafter referred to as a "reference spectra"), the system of the present invention may make a CLS comparison of reference spectra to the sample absorbance spectrum and make a determination as to the likelihood of the reference chemical being represented in the sample absorbance spectrum. FIG. 22 illustrates one manner in which the present invention makes such comparisons. In step 196, the system will define a search compound, which may be the first compound in the database. Once a search compound has been identified, the analytical range associated with that compound will next be identified. This analytical range will be defined based over which IR frequencies the compound evidences absorption. For example, FIG. 23a illustrates the analytical range for a hypothetical compound B, which possesses an analytical range consisting of two non-contiguous sets of infrared frequencies. Compound B's analytical range consists of the frequency segments B1 (810–850 cm$^{-1}$) and B2 (880–900 cm$^{-1}$). Since there is only one compound under consideration, the analytical range included in the design matrix (R1 and R2) will consist of these two non-contiguous sets of frequencies. However, the design matrix will also include columns for $H_2O$ and $CO_2$ if the analytical range of either of those compounds overlaps either R1 or R2. For example, if $H_2O$'s analytical range is 1300–850 cm$^{-1}$, then one column in D will consist of the $H_2O$ reference spectrum values for the two frequency ranges R1 and R2. Likewise, if $CO_2$'s analytical range is 650–750 cm$^{-1}$, then the design matrix for the compound B described above will not contain a column corresponding to $CO_2$. It is important to note that inclusion of $H_2O$ or $CO_2$ in the analysis does not affect the analytical range used in the analysis (i.e. the rows of the design matrix), but only the number of columns in the design matrix.

Associated with each compound that possesses at least one reference spectrum included in the database will be some number of analytical ranges, and these analytical ranges will also be stored in the database. The analytical ranges will be for the most part limited to contiguous subsets of the IR frequencies at which both the compound evidences absorption and the backdrop spectrum evidences favorable infrared intensity. The selection of the appropriate frequency subsets will involve, additionally, the set of frequencies over which other compounds included in the database evidence absorption; of these other compounds, H2O and CO2 are the most important, since their presence in ambient air is ubiquitous. However, several other types of compounds may also be of particular interest, those being compounds that are likely to be present in samples of interest, or that possess particularly intense absorption characteristics, or that possess particularly broad absorption patterns. The selection of the appropriate analytical ranges will also involve the intensity and uniqueness of the spectral absorption patterns of each compound. Further, for those compounds associated with two or more analytical ranges, the analytical ranges will be assigned a "rank" which distinguishes them from the other ranges associated with that compound, and these ranks will also be stored in the database. Spectral searches and CLS analyses will be adjusted to include all analytical ranges with ranks below an adjustable maximum rank. This practice will allow use of additional spectral data for the compound, as required, in the spectral searches and CLS analyses; such adjustments will be made in response to the quality of the spectral search results and/or CLS analysis results during both laboratory tests and field applications.

Figure 24:
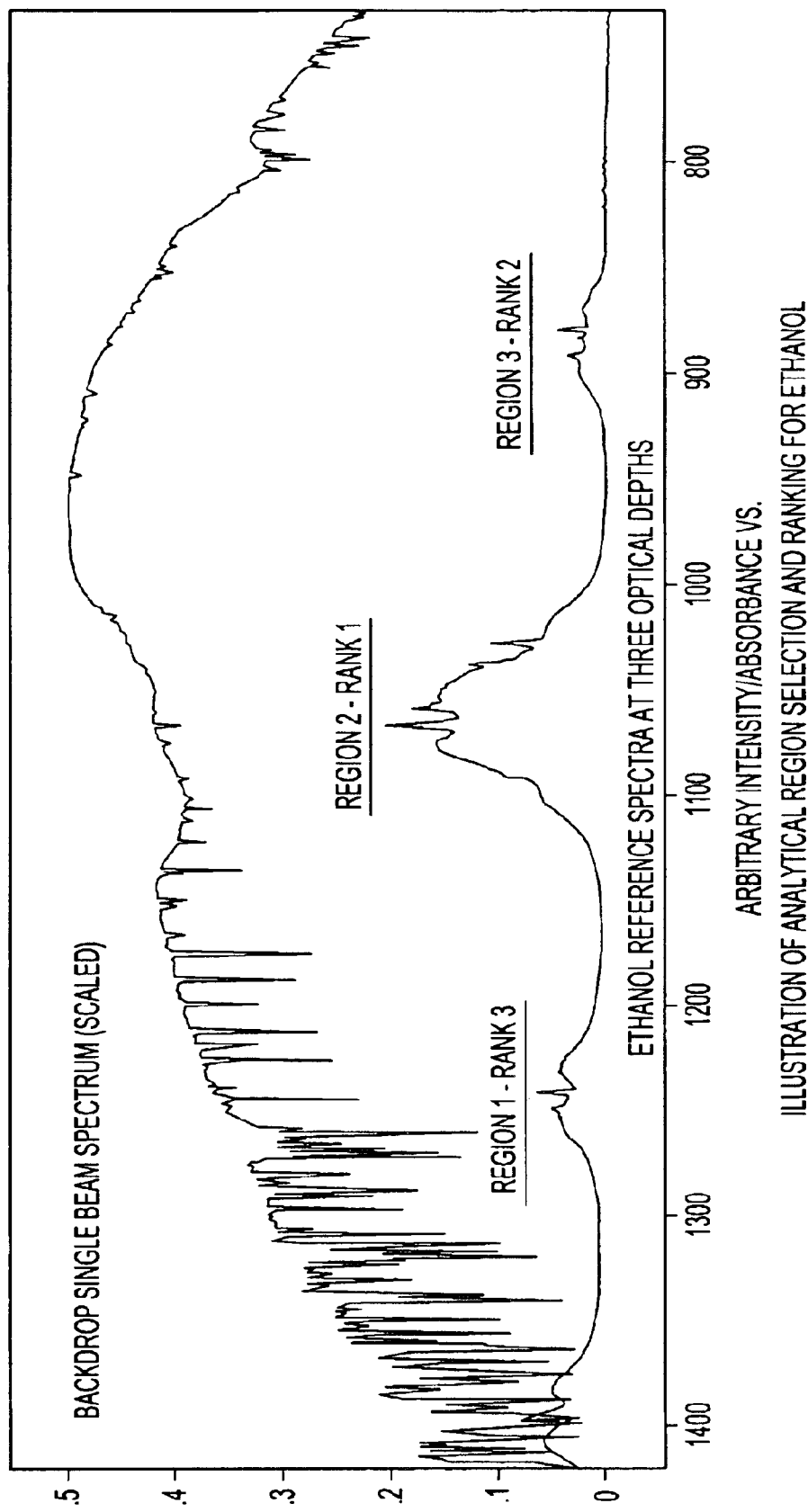
FIG. 24 illustrates the bases for analytical region selection and ranking.
Figure 25:
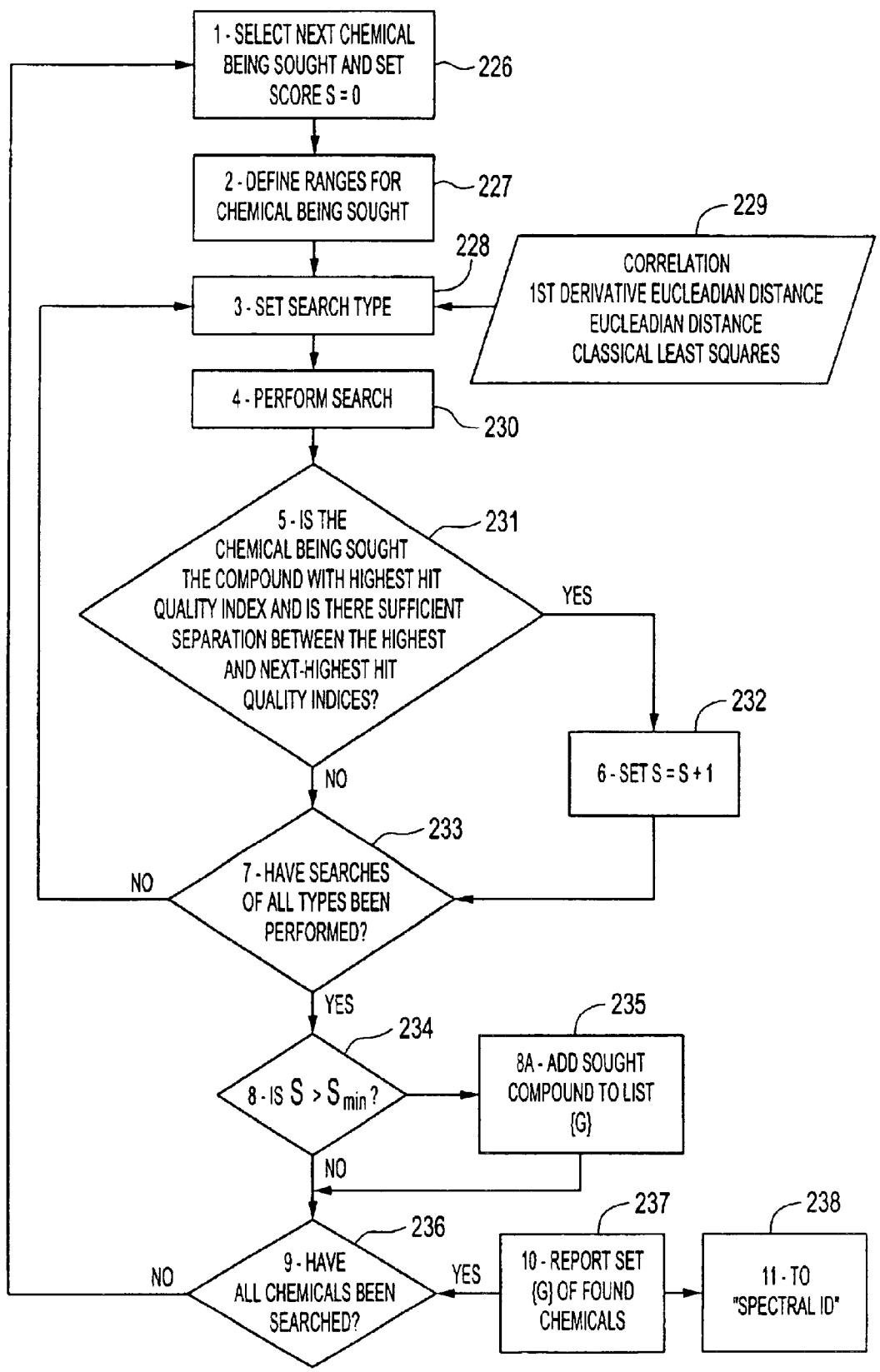
FIG. 25 is a flow chart illustrating the steps in a galactic spectrum search.

FIG. 24 illustrates a possible selection and ranking process for the compound ethanol. As seen in the lower trace, which represents ethanol's absorbance pattern, there are three distinct absorption bands, labeled Region 1 through Region 3, between 800 and 1300 cm$^{-1}$. Between these limits, the backdrop intensity varies, but is relatively constant. In contrast, the sharp H2O absorption features in the backdrop spectrum are seen to become more intense in the higher wavenumber portions of the spectrum. The combination of these factors indicates that, in the presence of water, Region 2 will yield the best analytical results for ethanol and that Region 1 will yield the poorest results. This leads to the "Rank 1" designation given Region 2, the "Rank 2" designation given Region 3, and the "Rank 3" designation given Region 1. In a preferred embodiment, the routine is set up to use only the Rank 1 region in the design matrix. However, the analytical routine could also be adjusted to include regions of both Ranks 1 and 2; or, it could even be adjusted to include all the ranks for this compound (1, 2 and 3). Moreover, those skilled in the art will recognize that every compound will potentially have any number of ranges and each assigned any rank. Thus, the present invention is not limited to the three-rank, one-region-for-each-rank example illustrated above.

Since the system is again utilizing a CLS comparison, the design matrix D for the CLS procedure must be defined as in step 197 of FIG. 22. At least one column of the design matrix will represent the reference spectrum for the compound selected (and multiple columns if multiple reference spectra are selected). The rows of the design matrix will only include only those infrared frequencies in the analytical range of the Search Compound. As this CLS analysis is not a WICLS analysis, the weight matrix is set equal to the identity matrix (P=I) as in step 198. The Parameter Estimates X, Residual V, Sum of Squared Errors $V^2$, and the Marginal Standard Deviations $\Delta$, for the search compound are calculated as described above in relation to equations 8–11 (step 199). The purpose of finding these values is that they can provide a "Quality Index" $Q_j$ which is indicative of the quality of a CLS determination for the parameter $\overline{X}_j$. Using the sample absorbance vector A from step 200, $Q_j$ may be defined as:

$$Q_j \equiv 100 \times (1 - R_j) = 100 \times \left(1 - \frac{\overline{\Delta}_j}{\overline{X}_j}\right) = 100 \times \left(1 - \frac{U_j^S}{\Theta_j^S}\right) \quad \text{Eq. (24)}$$

U and $\Theta$ are defined below and for now it only need be understood that in the present invention, CLS values of $\overline{X}_j$ with related quality indices $Q_j$ falling below specified values are referred to as "undetermined." The value of $Q_j$ below which a compound will be considered undetermined will vary for different CLS applications. One preferred embodiment of the present invention considers a $Q_j$ of less than 90 to be an undetermined value of $\overline{X}_j$. This decision is represented in step 201 of FIG. 22, where a $Q_J$ of greater than 90 is considered a positive ("determined") result (step 202) and a lower $Q_J$ is considered a negative ("undetermined") result (step 203). Finally, the results of this search are reported in step 204. Thus, this above described method, referred to herein as the "CLS Search", provides an example of one procedure for searching and identifying compounds which may be represented in a sample absorption spectrum.

Another method the present invention shall employ in making an initial identification of compounds is that developed by Thermo Galactic of Salem, N.H. While this method (the "Galactic search") is utilized in the present invention, the Galactic search itself is not the subject of the present invention. The Galactic search method (see FIG. 25) begins (step 226) with defining the analytical range for the chemical being compared to the sample spectrum (step 227). As in the method of FIG. 22, the Galactic search utilize a database which relates absorbance characteristics over given ranges for various chemical compounds. The system will correlate the absorption characteristics to the frequency ranges over which that compound absorbs IR energy. This "analytical range" will correspond to the compound which is being searched. Once the analytical range is determined, the Galactic search will employ a number of different algorithms in making a search determination. An important distinction between this search and that described in relation to FIG. 22 above is that the Galactic search does not include any data representing $CO_2$ or $H_2O$. As suggested in step 229 of FIG. 25, the Galactic search includes search types based upon correlation, first derivative, Eucleadian distance, and first derivative Eucleadian distance.

The Galactic search initially is set to begin searching with one of the particular search types listed above (step 228). The search will generate a list of all reference spectra in the database in the order of each reference spectrum's strength of correlation to the sample spectrum (step 230). If the reference spectrum for the compound selected is the first in ranking, and there is N percentage separation between the first and second ranking (step 231), then the compound selected is considered to have reliable result and a 1 is added to a reliability index associated with that compound (step 232). The degree of separation N may vary for different embodiments. By way of example the separation N could be zero percent in one embodiment, twenty-five percent in another, or any other percentage found to give accurate results. This method is then repeated for each of the five search types described above (step 233) and reliability index incremented (to a maximum possible value of 4) as the condition of step 231 is fulfilled. If the reliability index S is greater than a preset $S_{min}$ (step 234), then that compound is added to the list of compounds being generated by the search (step 235). Thereafter, this method is repeated for each compound in the Galactic database (step 236). The ultimate output of the Galactic search will be a list of each compound with a reliability index of at least 1 and the value of the compounds reliability index (step 237). This list is then sent to the search program discussed below in reference to FIG. 26 (step 238).

Figure 26:
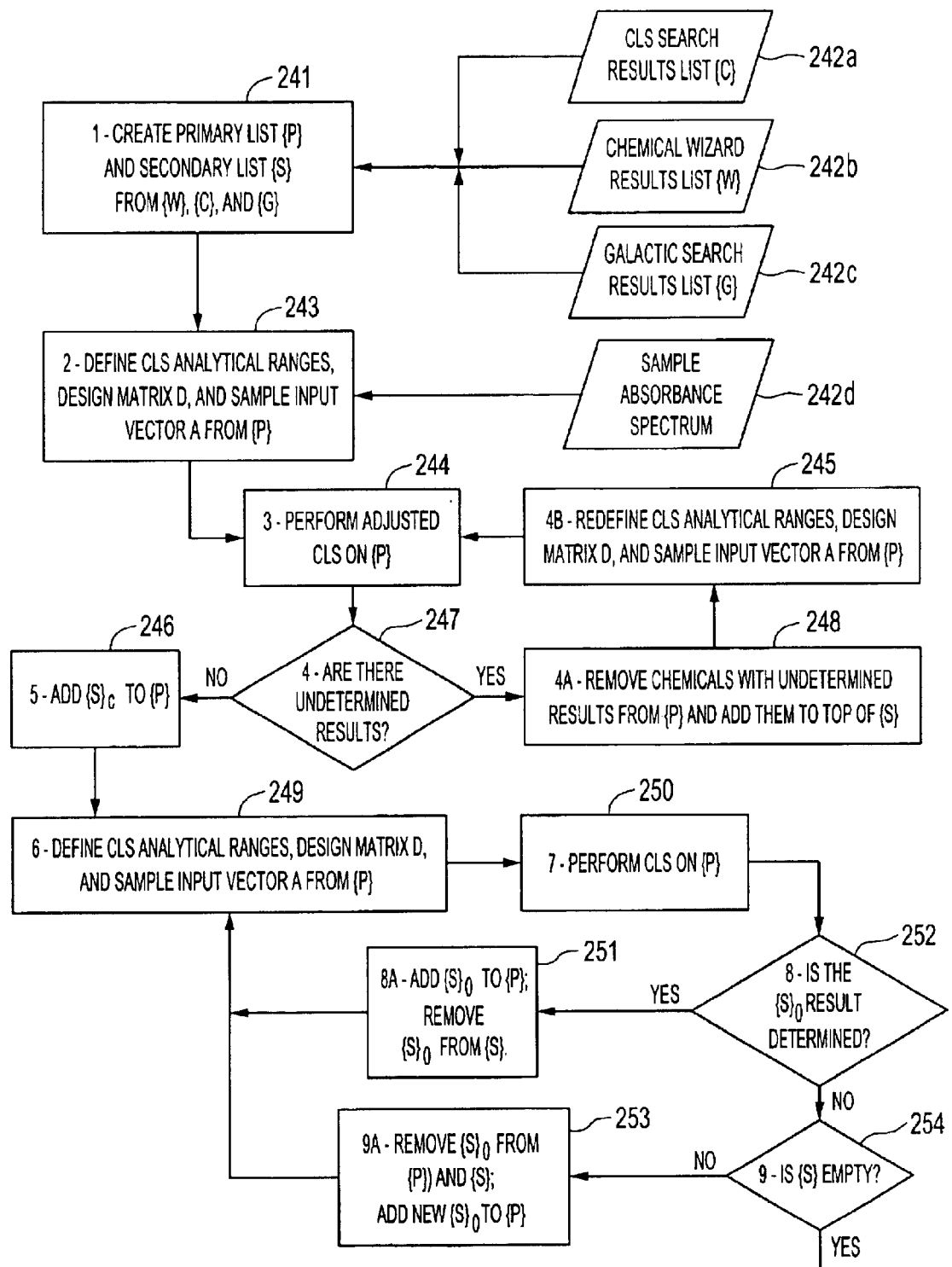
FIG. 26 is a flow chart illustrating the steps in another chemical identification spectral search.
Figure 26:
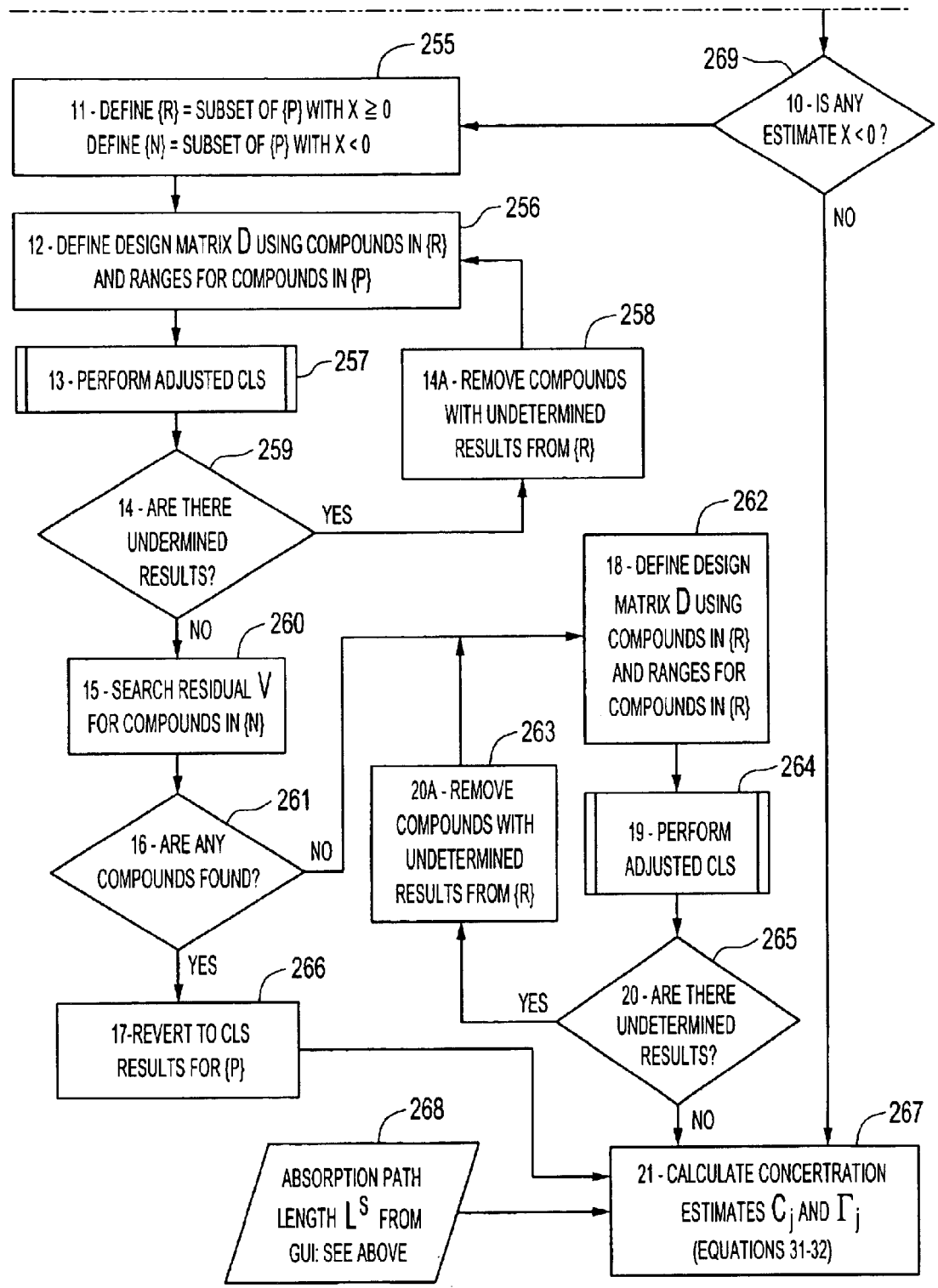

By employing the CLS Search, the Galactic Search and the Wizard Searches, the present invention will create an initial or tentative list of chemical compounds represented in the sample absorbance spectrum. The "Wizard Searches" refer to the compounds that the Chemical Properties Wizard, the Facilities Wizard, or the Railcar Wizard described above indicate are potentially present. The present invention will then process this initial list of compounds in a novel manner in order to determine with greater certainty which compounds from the initial list are most likely represented in the sample absorbance spectrum. FIG. 26 illustrates how the first step (241) in this process is to create a Primary List and a Secondary List based upon the correspondence of chemicals across these three search lists (242a–242c), which will be referred to below as by the designations {C} for the CLS Search list, {G} for the Galactic Search list, and {W} for the Wizard Search list.

Figure 23B:
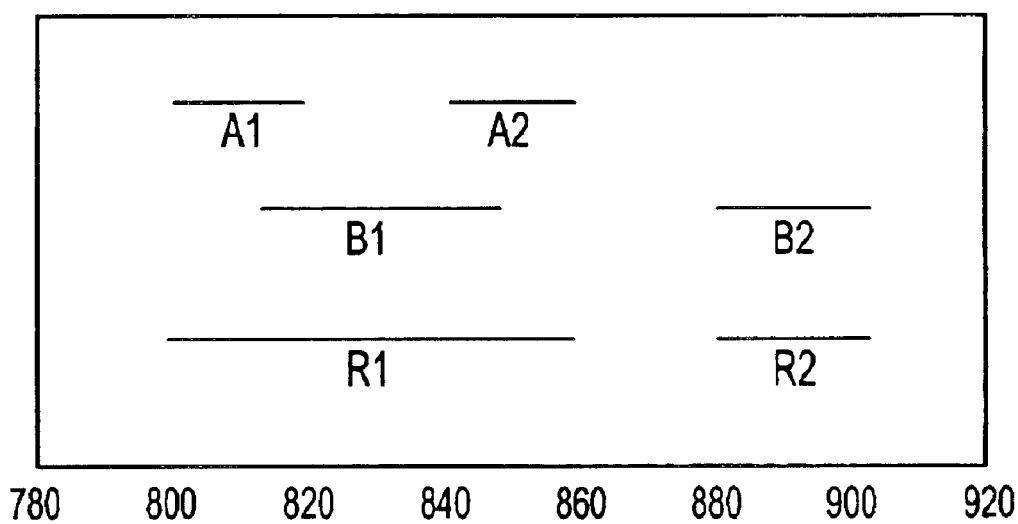

The primary list {P} comprises all compounds identified in list {C} plus those compounds which are found in both lists {W} and {G}. Expressed in set notation, {P} equals {C}∪{{W}∩{G}}. The set {S} is the complement of {P} within the overall union {C}∪{W}∪{G}. In other words, {S} represents any compound found in either lists {C}, {W}, or {G} and which is not already listed in {P}. The list {P} represents those compounds most likely to be represented in the absorbance spectrum while the list of compounds in {S} are considered less likely to be present in the sample, but require some spectroscopic attention. Next, in step 243, the system will define the CLS analytical range R, the design matrix D, and sample input vector A from {P}. The analytical range R is the union of the analytical ranges for all the compounds in {P} and as illustrated in FIG. 23b, is determined in a manner similar to that described above in reference to FIG. 23a. By way of example, if the list {P} has only the two compounds A and B (comprised of frequency ranges A1, A2 and B1, B2 respectively), then the analytical range R will be those IR frequencies over which any compound demonstrates absorbance. As before, the compounds $H_2O$ and $CO_2$ are also included in the analysis to the extent that their analytical ranges overlap those IR frequencies defined by {P}, but their frequency ranges are not otherwise used in defining R. The components of the vector A are the sample absorbance values over the analytical range R. The columns of D consist of the values for the reference spectra $A_{ij}^R$, and the wave number $v_i$, and $v_i^2$ over the same frequency range. The design matrix D will thus appear as:

$$D = \begin{pmatrix} A_{11}^R & A_{12}^R & . & A_{1M}^R & 1 & v_1 \\ A_{21}^R & A_{22}^R & . & . & 1 & v_2 \\ . & . & . & . & . & . \\ A_{N1}^R & A_{N2}^R & . & A_{NM}^R & 1 & v_N \end{pmatrix} \qquad \text{Eq. (25)}$$

It will be understood that each column in matrix D (except for the two rightmost) represent the reference spectra $A^R$ for a compound in list {P} over the analytical range $v_1$ to $v_N$.

Figure 27:
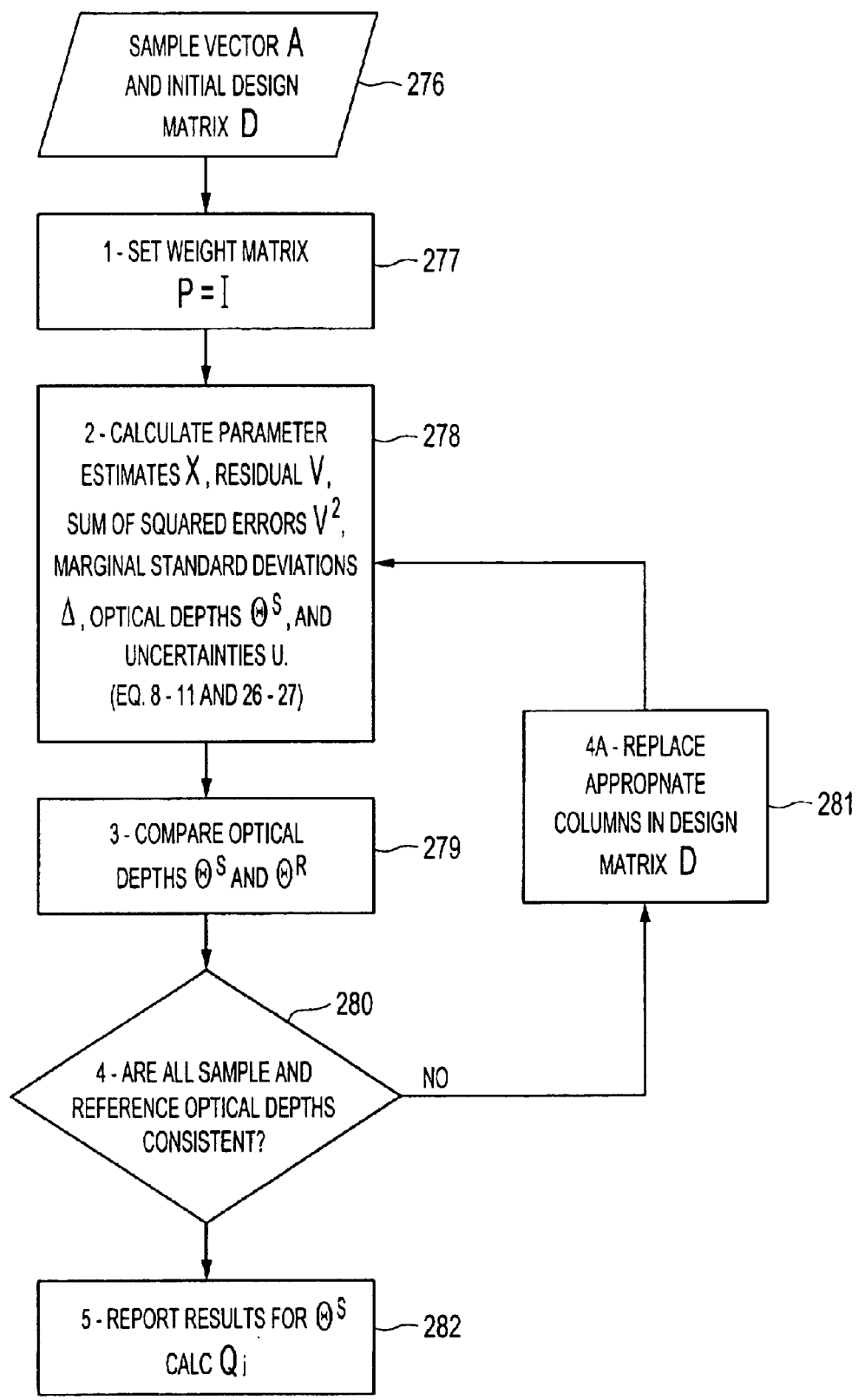
FIG. 27 is a flow chart illustrating the steps in an adjusted CLS procedure.

The next step in FIG. 26 (step 244) is to perform an "Adjusted CLS" analysis on the compounds of list {P}. FIG. 27 illustrates the steps taken in making an Adjusted CLS analysis. The sample vector A and design matrix D are define as immediately above (step 276). In step 277, the weight matrix P (see equations 5 and 6) is set to the identity matrix I (thus making this form of the CLS analysis an "unweighted" form). Step 278 next requires the calculation of Parameter Estimates $\overline{X}_j$, Residual V, Sum of Squared errors $V^2$, and Marginal Standard Deviations $\overline{\Delta}_j$ (see equations 7–11). The system also calculates Optical Depths $\overline{\Theta}_j^S$ and Uncertainties $\overline{U}_j^S$ using the following relationships:

$$\overline{\Theta}_j^S = \overline{X}_j \Theta_j^R \frac{p_j^R}{p^S} \frac{T^S}{T_j^R} \qquad \text{Eq. (26)}$$

Where:

$\Theta_j^R$ = optical depth (ppm-m value) of a single reference spectrum of the (pure) $j^{th}$ compound;

$T_j^R$ = absolute temperature (Kelvin) at which the $A_{ij}^R$ were recorded;

$p_j^R$ = absolute pressure (atmospheres) at which the $A_{ij}^R$ were recorded;

$T^S$ = absolute temperature (Kelvin) at which the $A_i^S$ were recorded;

$p^S$ = absolute pressure (atmospheres) at which the $A_i^S$ were recorded.

Similarly, the MSD (1σ uncertainty) in $\overline{\Theta}_j^S$ is denoted by $\overline{U}_j^S$ and given by $$\overline{U}_j^S = \overline{\Delta}_j \Theta_j^R \frac{p_j^R}{p^S} \frac{T^S}{T_j^R} \qquad \text{Eq. (27)}$$

Step 279 then compares the calculated optical depth $\overline{\Theta}_j^S$ for the sample spectrum and the given optical depth for the corresponding reference spectra $\Theta_j^R$. Optical Depth is an important parameter because its value, in combination with the optical path length through the gas being sampled, will provide estimates of the concentration of the compound. For many compounds, the infrared spectral database contains multiple reference spectra recorded at different optical depths, i.e. different concentrations. For such a compound, the most accurate available CLS result is that based on the specific reference spectrum for the compound which has the closest Optical Depth to that found in the sample gas, and this specific spectrum is not necessarily the same reference spectrum chosen for calculation of the initial design matrix D.

To account for this source of potential error, step 280 carries out the following analysis. It will be understood that for each compound, the current CLS result $\overline{\Theta}_j^S$ must fall in one of three categories: a) an $\overline{\Theta}_j^S$ below the reference spectrum for that compound with the lowest optical depth, or b) an $\overline{\Theta}_j^S$ between the optical depths of two of its reference spectra, or c) an $\overline{\Theta}_j^S$ above the reference spectrum with the highest optical depth. These three cases are described below. If the result is case (a), the current CLS results for the compound in question is consistent and no further action is required. If the result is case (b), then for a specific compound (j), it may be necessary to repeat the CLS analysis after replacing the corresponding column of the design matrix with values from a different reference spectrum of a different optical depth for that compound. Where $\Theta_{j\ LOW}^R < \overline{\Theta}_j^S \leq \Theta_{j\ HIGH}^R$, the following parameters may be defined:

$$\beta \equiv \frac{\overline{\Theta}_j^S}{\Theta_{j_{LOW}}^R} \text{ and } \gamma \equiv \frac{\overline{\Theta}_j^S}{\Theta_{j_{HIGH}}^R}. \qquad \text{Eq. 28}$$

In general, the CLS result can be defined as consistent according to any appropriate mathematical comparison of the values $\beta$ and $\gamma$; this definition may be compound-specific, and may require additional iterative constraints. For example, certain allowable ranges of values for $\beta$ and $\gamma$ could be predetermined (e.g. $0.5 \leq \beta \leq 5$ and $0.5 \leq \gamma \leq 5$) and this be used to judge whether a CLS result is consistent.

In an alternative embodiment, the results will be defined as inconsistent if the current reference spectrum does not posses the optical depth $\Theta_{j\ HIGH}^R$, and only one change of reference spectrum for any compound is allowed, regardless of the number of iterations required in the overall procedure. The procedure of FIG. 27 employs this embodiment which may be best understood with an example. Assume that three reference spectra—S1, S2, and S3—with optical depths D1=100 ppm-m, D2=250 ppm-m, and D3=500 ppm-m (respectively) are available for analyses of a particular compound. Then assume that the current CLS analysis employs the spectrum S3 and returns a result $\overline{\Theta}_j^S$=200 ppm-m. This results falls between D1 and D2, so $\Theta_{j\ LOW}^R$=D1=100 ppm-m and $\Theta_{j\ HIGH}^R$=D2=250 ppm-m. Using the standard given above, this is an inconsistent result because the results falls between D1 and D2, so one of the reference spectra associated with these optical depths (S1 or S2) is likely to provide a more reliable result that the reference spectrum (S3, with D3=500 ppm-m) used in the current CLS analysis. Step 280 in FIG. 27 performs this function and also checks whether previous results have been adjusted already. If not, the design matrix would be revised to include values from S2 (rather than the current S3), and the analysis would be repeated (step 281). If however, in a previous CLS analysis the design matrix has already been adjusted because of inconsistent results for this compound, further revisions would not be made, despite the inconsistent result yielded by the current CLS analysis. This practice is required to avoid the possibility of allowing the computer program to enter an infinite logical loop.

If the result is case (c), the current CLS result is consistent, but the result is flagged as a possible underestimate of the actual sample optical depth. Lastly, step 282 then performs a further calculation by determining the hit quality index, $Q_j$ (Equation 26).

Returning to FIG. 26, upon completion of the Adjusted CLS analysis in step 244, the results of greatest interest are the ppm-meter estimates $\overline{\Theta}_j^S$ and their related (new) quality indices $Q_j$. All compounds with a $Q_j$ of less than some selected value (typically near 90 in a preferred embodiment) are considered "undetermined." (step 247) If there are undetermined results, step 248 will remove the chemicals with undetermined results from list {P} and add those compounds to the top of list {S}. Using the new shortened list {P}, step 245 redefines the CLS analytical ranges R, the design matrix D, and the sample input vector A in a manner similar to Step 243. The iterative process of steps 244 and 247 is then continued until the results for all the compounds in {P} are determined.

When there are no further undetermined results, step 246 will add the first compound {S}$_0$ at the top of list {S} to the latest list {P} and remove {S}$_0$ from {S}. With the new list {P}, the CLS analytical ranges R, the design matrix D, and the sample input vector A are redefined in step 249 and another Adjusted CLS analysis on the new list {P} is carried out in step 250. If the most recently added {S}$_0$ compound is determined in step 252, step 251 will add the next {S}$_0$ to list {P} (and remove {S}$_0$ from {S}) and step 249 will be repeated. If in step 252 the {S}$_0$ compound is undetermined, then step 254 will determine whether {S} is empty. If not, step 253 will remove {S}$_0$ from both lists {P} and {S} and adds the next top compound {S}$_0$ of list {S} to list {P}. This process is continued until {S} found to be empty in step 254.

Before making a final determination as to which compounds the system identifies as represented in the sample spectrum, a determination will be as to whether any compound is an IR emitter. Step 269 questions whether any Estimate $\overline{X}_j<0$. If all the CLS results (and related ppm-meter estimates $\overline{\Theta}_j^S$) are zero or positive, the last step in the analysis will be to calculate the concentration estimates Cj and Γj as described below. If there are negative estimates of $\overline{X}_j$, then steps 255 through 265 are performed to determine whether these suspected emitters are spurious results or if there is actual evidence in the sample of that compounds are emitting IR radiation. Step 255 will define {R} as a subset of {P} were X>0 and will define {N} as the subset of {P} were X<0. The set {R} contains those compounds that the last CLS analysis of {P} indicated as infrared absorbers in the sample, and {N} contains those compounds indicated as infrared emitters. Step 256 will define a new design matrix D from {R} without range redefinition (i.e., using the last range found in the last iteration of step 249). The columns of matrix D thereby correspond to only those compounds indicated as infrared absorbers in the sample, but the spectral range corresponds to all the compounds found to have well determined CLS results in Steps 241–254. Step 257 will perform Adjusted CLS on {R} in the same manner as above. If there are undermined results, step 258 removes the undetermined compounds and steps 256–259 are repeated until there are no undetermined results. Thereafter, step 260 will search the residual V for Chemicals in the Set {N}. If the compounds indicated as infrared emitters (see Step 269) are actually present as such in the sample, then the residual matrix V should contain evidence of them, so the residual is subjected to the spectral searches preceding Step 1 (i.e. Galactic and CLS Search).

Step 261 determines whether any chemicals in set {N} are found. If yes, then residual spectrum contains a recognizable pattern of at least one compound included in the database but excluded from the CLS analysis used to generate the residual. The presence of such a recognizable pattern indicates that at least one absorbing or emitting compound not included in the analysis is likely to be present in the sample. In this case, the results of Steps 241 through 254 using the set {P} are the best available, and step 266 reverts to the results for set {P} identified at the point of step 254. If the search in step 261 does not indicate the presence of any compounds from set {N}, then all the negative results in Steps 241 through 254 are considered spurious. The current set of compounds {R} is considered accurate, but the current analytical range needs to be reduced, so the method proceeds to steps 262–265. In step 262, the design matrix D is redefined using compounds in {R} and ranges for compounds in {R}. Adjusted CLS is then performed using this redefined range. If there are undetermined results in step 265, then the compounds with undetermined results are removed in step 263 and the process returns to Step 262. If there are no undetermined results, then the current results are considered final and are forwarded to step 267.

As a final step in the process of identifying chemical compounds, the present invention will determine the concentration $C_j$ for each compound and the uncertainty $\Sigma_j$ associated with that concentration measurement. These values may be calculated from the equations:

$$C_j = \frac{\overline{\Theta}_j}{L_S F_T} \quad \text{Eq. (29)}$$

and $$\Gamma_j = \frac{\overline{U}_j}{L_S |F_T|} \quad \text{Eq. (30)}$$

Figure 28:
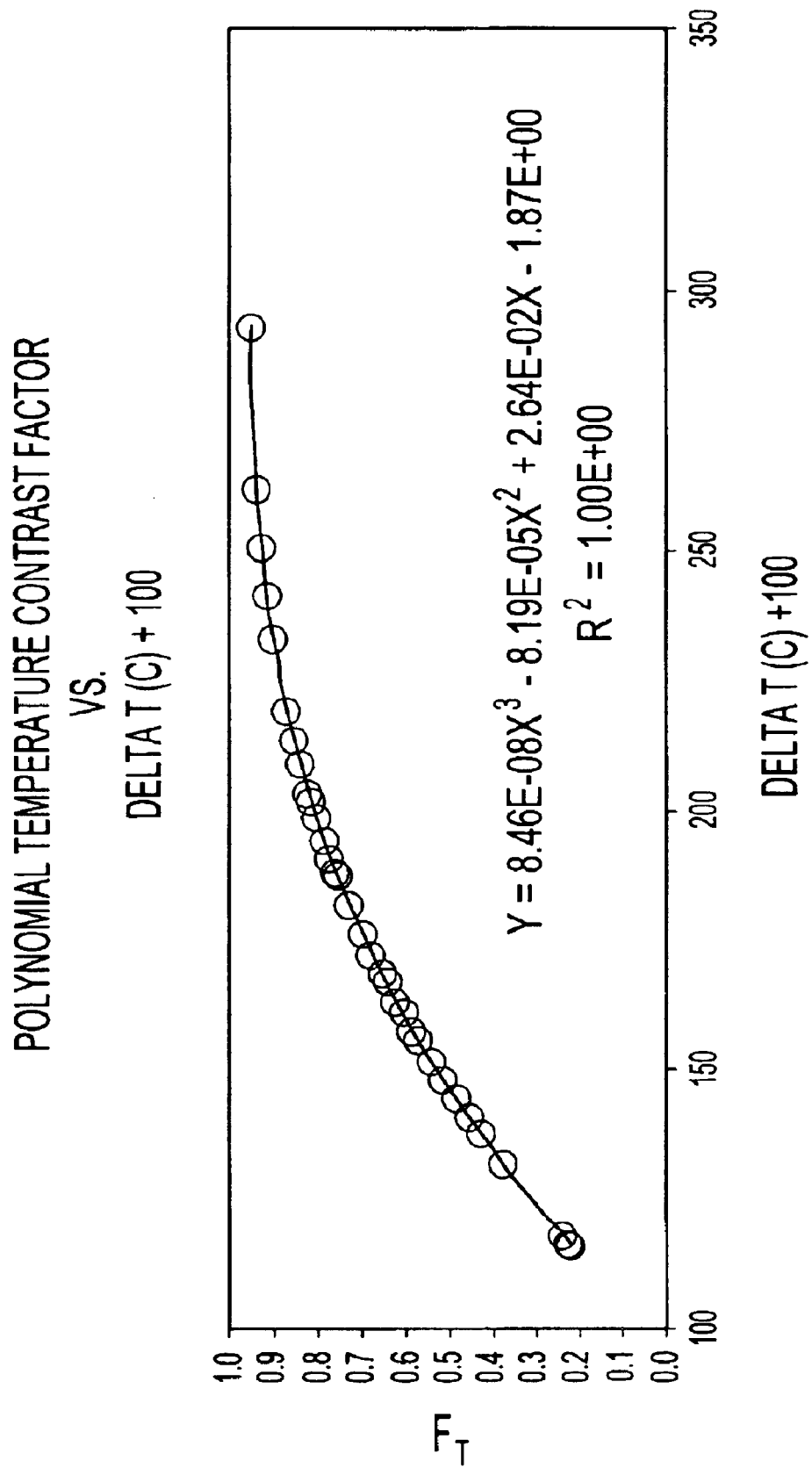
FIG. 28 is a curve illustrating contrast division factors vs. temperature contrasts.

The quantity $F_T$ in Equations 29 and 30 is a correction factor describing the variation of the observed absorbance of ethylene with the temperature contrast $\Delta T = T_A - T^0{}_B$. FIG. 28 illustrates the measured variation and the third order polynomial regression used in this work to define $F_T$. It can be seen that the sample absorption pathlength $L_S$ must be known. Generally $L_S$ will be estimated by the user and input into the system during the initial measurements described in reference to step 127 in FIG. 13 (step 268).

Figure 29:
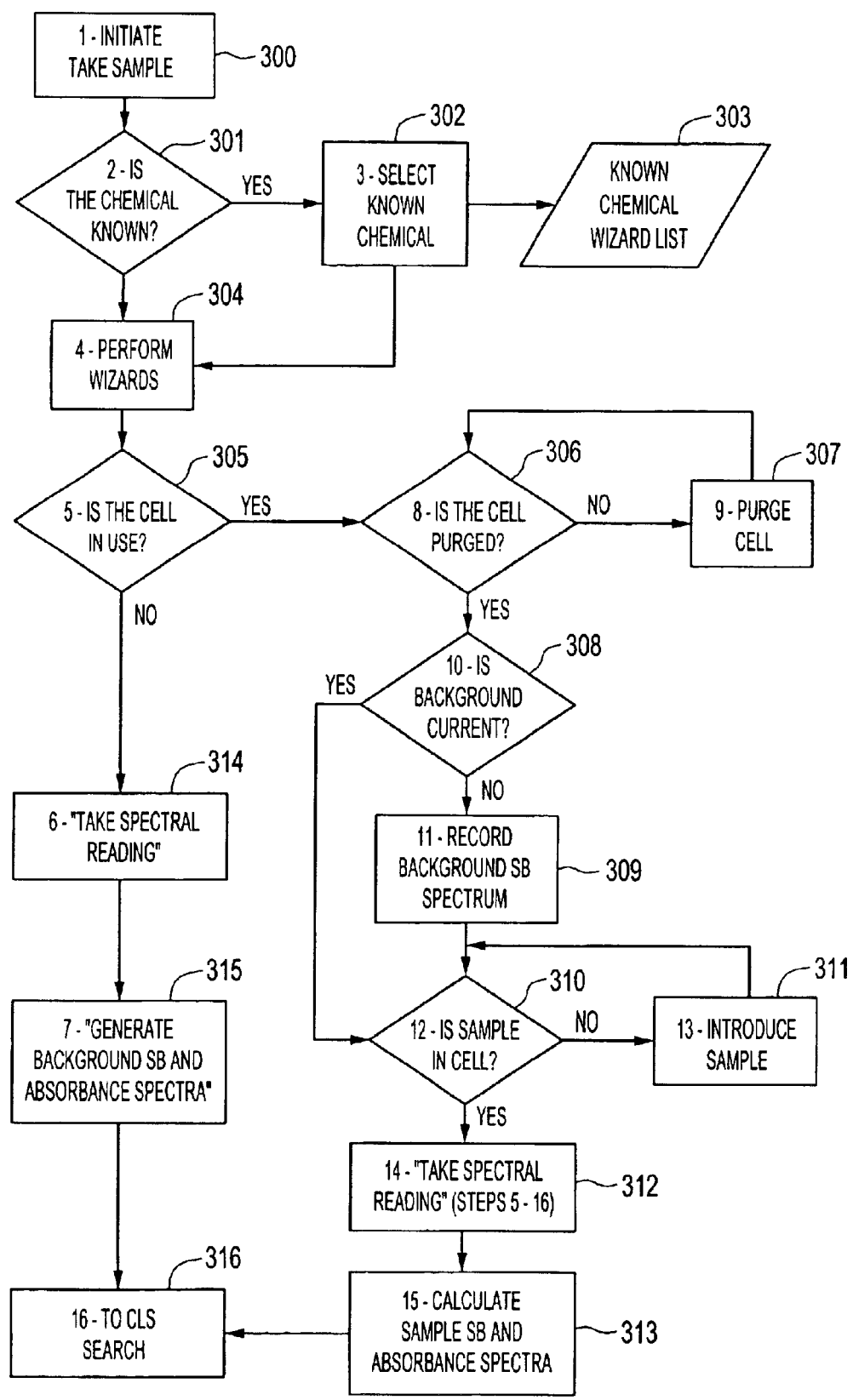
FIG. 29 is a flow chart illustrating the steps in the sample taking routine employed by the present invention.

FIG. 29 illustrates certain additional functionalities performed by the software of the present invention. Part of the routine will involve obtaining a spectrometer reading of a gas contained in a glass sample bottle or "cell". Taking a reading of a gas sample in a cell is procedure well known in the art. However, several of the steps, including steps 300–305 and 314–316 may be carried out independently of whether a gas cell is being utilized. Step 300 will initiate the routine and identify it for the user. Step 301 will query the user whether he or she knows what chemical compound is to be identified with the spectrometer. This contemplates the situation where a user arrives at the scene of a chemical release with prior information concerning what compounds (particularly toxic or otherwise dangerous compounds) may have been release. The user may wish to immediately take spectrometer readings in several different directions to determine if the presence of the suspected chemical can be identified. To this end, step 302 will query the user to select a known or suspected chemical with 303 presenting an alphabetical listing of all chemical compounds in the database on touch screen 11 (FIG. 4). Once the known compound is selected, step 302 will return the reference spectra for that compound to step 305. The principle behind selecting the known or suspected compound is to greatly identify the spectral identification process. If the identification software need only compare a spectral reading to one particular reference spectrum, a confirmation of the existence of that particular compound can be made considerably quicker. The user will take a spectral reading in step 314 (described in detail in FIG. 13), generate a background SB and absorbance spectrum in step 315 (see FIG. 18) and then in step 316 branch to the CLS search of FIG. 22. After performing the CLS search, the results will be sent to the routine shown in FIG. 26. Rather than lists 242a–242d providing multiple spectra, there is only one reference spectrum in lists 242a–242c. This reference spectrum (along with those of the ubiquitous compounds $H_2O$ and $CO_2$) is processed as described above in reference to FIG. 26. The output of this determination will inform the user whether the known compound was detected by the spectrometer.

Returning to step 305, if the user determines that he wishes to utilize the gas cell (i.e. capture a sample of the gas in the cell and then spectrally analyze the gas within the cell), the program will advance to step 306 and enquire as to whether the gas cell has been purged (i.e. flushed with an inert gas such as nitrogen to remove any remnants of a previous use. If no, the user is instructed to purge the gas cell or if the spectrometer is properly equipped with the additional hardware to perform this function automatically, the spectrometer may do so. When the gas cell has been purged, the software will query whether the background spectrum is current. It should be understood that when a spectral reading of a sample in a gas cell is taken, a known source of predetermined background radiation is utilized. This is possible because the gas sample is contain in the gas cell which can be easily positioned at any distance between a spectrometer and a radiation source of the user's choosing. This is clearly not the same routine used when estimating a background based upon a remote source as discussed above in reference to FIG. 18. If the background is current (i.e. the conditions under which the background was obtain have not changed), the program will move to step 310. If the background is not current, a new background SB spectrum will be taken. This typically entails filling the cell with an inert gas such as nitrogen and recording the spectrum obtained when the cell is placed in front of the radiation source. Step 310 will query whether the gas sample is in the cell. If not the program will instruct the user to introduce the gas sample or if the spectrometer is equipped with the proper external hardware, the program will automatically open the valve on the gas cell and a sample of the surrounding air will be drawn into the cell. Steps 312 and 313 will then take a spectral reading of the gas in the cell and generate the single beam spectra (see FIG. 13) and absorbance spectra (see equation 1) related to the gas in the cell. Thereafter, the program will in step 316 branch to the routines of FIGS. 22 and 26 as described above. It will be understood that steps 306 to 313 are generally known in the art and do not in and of themselves form part of the present invention.

While the foregoing disclosure has described the invention in terms of specific embodiments, those skilled in the art will recognize many modifications which fall within the scope of the present invention. For example, while the different "Wizard" routines are described as being used in conjunction with spectral identification of chemicals, it is contemplated that the Wizards could be used by themselves (i.e. involving no spectral component) to provide a useful preliminary identification of a unknown chemical compound. All such modifications and variations are intended to come within the scope of the following claims.

We claim:

1. A method of generating a background spectrum for use in spectral analysis, said method comprising the steps of:
   a. providing a sample spectrum and an estimated temperature of a background object;
   b. from a set of known temperature spectra related to a known background temperature, selecting at least two known temperature spectra representing a background temperature above and below said estimated temperature;
   c. comparing said sample spectrum to said known temperature spectra in order to determine a sample background spectra.

2. The method of claim 1, wherein said step of comparing said sample spectra to said known temperature spectra further comprises the step of using classical least squares analysis.

3. The method of claim 1, wherein said estimated temperature is determined by a method comprising the steps of:
   a. providing a predetermined relationship between a parabolic center frequency and a backdrop temperature, wherein said parabolic center frequency is that of a single beam spectrum of a reference backdrop at a known temperature;
   b. providing a sample spectra recorded against a backdrop of an unknown temperature;
   c. determining a best fit parabolic curve of said sample spectra;
   d. determining a sample parabolic center frequency of said best fit parabolic curve;
   e. comparing said sample parabolic center frequency to said predetermine relationship of center frequency and backdrop temperature;
   f. estimating a temperature of said backdrop based upon said comparison.

4. The method of claim 3, wherein said step of determining a best fit parabolic curve further comprises the step of using classical least squares analysis.

5. The method of claim 4, wherein said step of using classical least squares analysis further comprises the step of using a weight iterative classical least squares analysis.

6. The method of claim 5, wherein weight iterations are continued until a fractional change in a sum of squared errors is less than a predetermined fraction.

7. A method of generating a temperature compensated absorbance spectrum, said method comprising the steps of:
   a. providing a sample spectrum and an estimated temperature of a backdrop object;
   b. from a set of known temperature spectra related to a known background temperature, selecting at least two known temperature spectra representing a background temperature above and below said estimated temperature;
   c. comparing said sample spectrum to said known temperature spectra in order to determine a sample background spectrum;
   d. calculating an absorbance spectrum from said sample spectrum and said background spectrum.

8. The method of claim 7, further comprising the step of comparing said absorbance spectrum to at least one chemical reference spectrum in order to identify a chemical represented in said absorbance spectrum.

9. The method of claim 8, wherein said step of comparing further includes using the spectra for CO2 and H2O in order to identify said chemical.

10. A method of identifying a chemical represented in an absorbance spectrum, said method comprising the steps of:
    a. providing a sample absorbance spectrum;
    b. comparing said absorbance spectrum to the analytical frequency range for CO2 and H2O and a plurality of chemical reference spectra in order to identify a chemical represented in said absorbance spectrum; and
    c. wherein said plurality of chemical reference spectra comprise a primary set of chemical reference spectra and said primary set of chemical reference spectra is formed from a plurality of chemical spectra identification methods.

11. The method of claim 10, further providing a chemical database associating predefined characteristics and properties with a plurality of chemical compounds, wherein at least one chemical reference spectra is identified by said database for inclusion in said primary set.

12. The method of claim 10, further providing a chemical/location database associating at least one chemical compound with an assigned map location of said compound, wherein at least one chemical reference spectra is identified by said chemical/location database for inclusion in said primary set.

13. The method of claim 12, wherein a user location is provided by a global positioning system.

14. The method of claim 13, wherein said assigned map location in said database is in a street address format.

15. The method of claim 13, wherein said user location is provided in a longitude/latitude format and compared to said database.

16. The method of claim 15, further identifying all compounds in said database which are within a predetermined radius of said user location.

17. The method of claim 10, further providing a container database associating predetermined container shapes with a set of compounds and a user interface, wherein said user interface displays container shapes for selection by a user and selection of a container shape identifies at least one chemical reference spectrum for inclusion in said primary set.

18. The method of claim 10, further providing a placard database associating a predetermined placard with a set of compounds and a user interface, wherein said user interface displays placard information for selection by a user and selection of a placard identifies at least one chemical reference spectrum for inclusion in said primary set.

19. A method of identifying a chemical represented in an absorbance spectrum, said method comprising the steps of:
    a. providing a sample absorbance spectrum;
    b. comparing said absorbance spectrum to the analytical frequency range for CO2 and H2O and a plurality of chemical reference spectra in order to identify a chemical represented in said absorbance spectrum; and
    c. wherein said plurality of chemical reference spectra comprise a primary set of chemical reference spectra and said comparison of said primary set of chemical reference spectra to said absorbance spectrum includes the steps of:

i. making a comparison of said primary set of chemical reference spectra to said absorbance spectrum;

ii. determining whether there are undetermined results for any of said reference spectra in said comparison;

iii. if undetermined results do exist in said comparison, then removing said reference spectra having undetermined results in said primary set;

iv. making another comparison of said primary set of chemical reference spectra to said absorbance spectrum;

v. repeating steps b–d until no undetermined results exist.

20. The method of claim 19, wherein after step (v), further taking a new reference spectrum from a secondary set of chemical reference spectra and adding said new reference spectrum to said primary set.

21. The method of claim 20, wherein steps (ii)–(iv) are repeated until no undetermined results exist in said primary step.

22. The method of claim 21, wherein said step of moving a new reference spectrum from said secondary set to said primary set is repeated until said secondary set is empty.

23. The method of claim 21, wherein said comparisons comprise a classical least squares analysis.

24. The method of claim 23, wherein all negative scaling factor values associated with a reference spectrum form a residual set.

* * * * *